(12) United States Patent
Yamada et al.

(10) Patent No.: US 12,740,702 B2
(45) Date of Patent: Sep. 22, 2026

(54) OPHTHALMIC OBSERVATION APPARATUS, METHOD OF CONTROLLING THE SAME, AND RECORDING MEDIUM

(71) Applicant: Topcon Corporation, Tokyo (JP)

(72) Inventors: Kazuhiro Yamada, Tokyo (JP); Kazuhiro Oomori, Tokyo (JP); Yasufumi Fukuma, Wako (JP)

(73) Assignee: TOPCON CORPORATION, Tokyo (JP)

(*) Notice: Subject to any disclaimer, the term of this patent is extended or adjusted under 35 U.S.C. 154(b) by 366 days.

(21) Appl. No.: 18/033,821

(22) PCT Filed: Dec. 9, 2020

(86) PCT No.: PCT/JP2020/045754
§ 371 (c)(1),
(2) Date: Apr. 26, 2023

(87) PCT Pub. No.: WO2022/091428
PCT Pub. Date: May 5, 2022

(65) Prior Publication Data
US 2023/0397810 A1 Dec. 14, 2023

Related U.S. Application Data

(60) Provisional application No. 63/106,087, filed on Oct. 27, 2020.

(51) Int. Cl.
*A61B 3/13* (2006.01)
*A61B 3/117* (2006.01)
(Continued)

(52) U.S. Cl.
CPC ................ *A61B 3/13* (2013.01); *A61B 3/117* (2013.01); *A61B 3/12* (2013.01); *A61B 3/14* (2013.01);
(Continued)

(58) Field of Classification Search
CPC .. A61B 3/13; A61B 3/14; A61B 3/145; A61B 3/152; A61B 3/117; A61B 3/12;
(Continued)

(56) References Cited

U.S. PATENT DOCUMENTS 5,579,772 A 12/1996 Kinukawa et al.
10,251,783 B2 4/2019 Chernyak
(Continued)

FOREIGN PATENT DOCUMENTS

CN 101268928 A 9/2008
CN 103784117 A 5/2014
(Continued)

OTHER PUBLICATIONS

Japanese Office Action issued Aug. 20, 2024, in corresponding Japanese Application No. JP 2022-558821, 6pp.
(Continued)

*Primary Examiner* — Stephone B Allen
*Assistant Examiner* — Jennifer A Jones
(74) *Attorney, Agent, or Firm* — XSENSUS LLP

(57) ABSTRACT

An ophthalmic observation apparatus according to an embodiment example includes a moving image generating unit, an analyzing processor, and a display controller. The moving image generating unit is configured to generate a moving image by photographing a subject's eye into which an artificial object has been inserted. The analyzing processor is configured to analyze a still image included in the moving image to identify a first site image corresponding to a predetermined site of the subject's eye and a second site image corresponding to a predetermined site of the artificial object. The display controller is configured to display, on a display device, the moving image, first position information
(Continued)

that represents a position of the first site image, and second position information that represents a position of the second site image.

7 Claims, 16 Drawing Sheets

(51) Int. Cl.
*A61B 3/12* (2006.01)
*A61B 3/14* (2006.01)
*A61B 3/15* (2006.01)
*A61B 90/00* (2016.01)
*G02B 21/00* (2006.01)
*G02B 21/36* (2006.01)
*G06T 7/00* (2017.01)
*H04N 23/67* (2023.01)
*H04N 23/71* (2023.01)
*H04N 23/74* (2023.01)
*H04N 23/76* (2023.01)

(52) U.S. Cl.
CPC ................ *A61B 3/145* (2013.01); *A61B 3/15* (2013.01); *A61B 3/152* (2013.01); *G02B 21/0012* (2013.01); *G02B 21/365* (2013.01); *G06T 7/0012* (2013.01); *G06T 7/97* (2017.01); *H04N 23/67* (2023.01); *H04N 23/71* (2023.01); *H04N 23/74* (2023.01); *H04N 23/76* (2023.01); *A61B 2090/0807* (2016.02); *G06T 2207/10016* (2013.01); *G06T 2207/10056* (2013.01); *G06T 2207/30041* (2013.01); *G06T 2207/30168* (2013.01)

(58) Field of Classification Search
CPC . A61B 3/15; A61B 2090/0807; A61B 3/0025; A61B 3/10; G02B 21/0012; G02B 21/365; G06T 7/97; G06T 7/0012; G06T 2207/10016; G06T 2207/10056; G06T 2207/30041; G06T 2207/30168; H04N 23/67; H04N 23/71; H04N 23/74; H04N 23/76
See application file for complete search history.

(56) References Cited

U.S. PATENT DOCUMENTS 10,369,053 B2 8/2019 Srinivasan et al.
2002/0026179 A1 2/2002 Toh
2004/0004694 A1 1/2004 Sugino et al.
2005/0073647 A1 4/2005 Mihashi et al.
2006/0247659 A1 11/2006 Moeller et al.
2007/0047072 A1 3/2007 Zimmer
2008/0123053 A1 5/2008 Mihashi et al.
2008/0198219 A1 8/2008 Yoshida et al.
2009/0122398 A1 5/2009 Machida et al.
2009/0190092 A1 7/2009 Tsukada et al.
2009/0244483 A1 10/2009 Yoshino et al.
2011/0122365 A1 5/2011 Kraus et al.
2011/0153013 A1 6/2011 Moeller et al.
2011/0157553 A1 6/2011 Moeller et al.
2011/0230751 A1* 9/2011 Kersting .............. A61B 3/0025 600/407
2011/0292340 A1* 12/2011 Shimizu ................ A61B 3/117 351/206
2011/0304819 A1* 12/2011 Juhasz ..................... A61B 3/13 351/205
2012/0050672 A1 3/2012 Aikawa
2012/0197102 A1 8/2012 Hanebuchi et al.
2013/0110092 A1 5/2013 Yee
2013/0110093 A1 5/2013 Yee
2013/0110206 A1 5/2013 Yee et al.
2013/0116672 A1 5/2013 Yee
2013/0135582 A1 5/2013 Hanebuchi et al.
2014/0118687 A1 5/2014 Ohban et al.
2014/0146287 A1 5/2014 Ota
2014/0160429 A1 6/2014 Nakano et al.
2014/0228824 A1 8/2014 Yee et al.
2014/0300863 A1 10/2014 Fukuma et al.
2015/0046094 A1 2/2015 Chaudhary et al.
2015/0077528 A1 3/2015 Awdeh
2015/0272435 A1 10/2015 Ito et al.
2015/0342460 A1 12/2015 Izatt et al.
2016/0095752 A1* 4/2016 Srinivasan .......... A61F 9/00834 606/6
2016/0128871 A1 5/2016 Yee
2016/0157710 A1 6/2016 Tomatsu et al.
2016/0228295 A1 8/2016 Yee et al.
2016/0291257 A1 10/2016 Huang et al.
2017/0151089 A1* 6/2017 Chernyak ............ A61B 3/0025
2017/0280989 A1 10/2017 Heeren
2017/0281405 A1 10/2017 Ha
2017/0303782 A1 10/2017 Ito et al.
2017/0304119 A1 10/2017 Yee
2018/0049840 A1* 2/2018 Awdeh ................... A61B 90/20
2018/0098812 A1* 4/2018 Ootsuki ................. A61B 90/25
2018/0125361 A1 5/2018 Okuda
2018/0228431 A1 8/2018 Chaudhary et al.
2019/0076012 A1 3/2019 Kobayashi
2019/0091008 A1 3/2019 Ishikawa
2019/0104921 A1 4/2019 Yamamoto
2019/0192251 A1 6/2019 Kado et al.
2019/0357980 A1 11/2019 Andrews et al.
2020/0146885 A1 5/2020 Ootsuki et al.
2020/0214562 A1 7/2020 Kawasaki et al.
2020/0237213 A1 7/2020 Ono et al.
2020/0306002 A1 10/2020 Kamata
2020/0311918 A1 10/2020 Loerner
2021/0401369 A1 12/2021 Chaudhary et al.
2022/0115122 A1 4/2022 Enoki et al.
2022/0148165 A1 5/2022 Ootsuki et al.
2022/0386869 A1 12/2022 Ono et al.

FOREIGN PATENT DOCUMENTS

CN 104939802 A 9/2015
DE 202013011877 U1 9/2014
EP 3491996 A1 6/2019
JP 2001-276111 A 10/2001
JP 3354627 B2 12/2002
JP 2003-310556 A 11/2003
JP 2006136714 A 6/2006
JP 2006280612 A 10/2006
JP 2007-028295 A 2/2007
JP 2009-118955 A 6/2009
JP 2011191517 A 9/2011
JP 2011528592 A 11/2011
JP 2012506272 A 3/2012
JP 2012152469 A 8/2012
JP 2013-027672 A 2/2013
JP 2014-068766 A 4/2014
JP 2014-534011 A 12/2014
JP 2016-182262 A 10/2016
JP 2016531666 A 10/2016
JP 2016209291 A 12/2016
JP 2016214781 A 12/2016
JP 2017-012430 A 1/2017
JP 2017029333 A 2/2017
JP 2018-051210 A 4/2018
JP 2018051223 A 4/2018
JP 2019-013803 A 1/2019
JP 2019-092844 A 6/2019
JP 2019-162336 A 9/2019
JP 2020-116140 A 8/2020
JP 2020-130607 A 8/2020
WO 03/022138 A1 3/2003
WO 2016061454 A1 4/2016
WO 2017/154348 A1 9/2017
WO 2017175853 A1 10/2017
WO 2017/221507 A1 12/2017

(56) References Cited

FOREIGN PATENT DOCUMENTS

WO 2018/207466 A1 11/2018
WO 2019/059314 A1 3/2019
WO 2020/179588 A1 9/2020

OTHER PUBLICATIONS

Japanese Office Action issued Sep. 3, 2024, in corresponding Japanese Application No. JP 2022-558822, 6pp.
Japanese Office Action issued Oct. 22, 2024, in corresponding Japanese Application No. JP 2022-558823, 6pp.
Japanese Office Action issued Aug. 27, 2024, in corresponding Japanese Application No. JP 2022-558830, 6pp.
Extended European Search Report issued Sep. 18, 2024, in corresponding European Application No. 21885560.9, 8pp.
Japanese Office Action issued Jun. 18, 2025, in corresponding Japanese Patent Application No. 2022-558823, 6pp.
Extended European Search Report issued Nov. 5, 2024, in corresponding European Patent Application No. 20959942.2, 8pp.
Extended European Search Report issued Nov. 7, 2024, in corresponding European Patent Application No. 20959943.0, 8pp.
Extended European Search Report issued Nov. 5, 2024, in corresponding European Patent Application No. 20959945.5, 9pp.
Chinese Office Action issued Dec. 20, 2024, in corresponding Chinese Patent Application No. 202080106764.2, 15pp.
Chinese Office Action issued Dec. 24, 2024, in corresponding Chinese Patent Application No. 202080106762.3, 18pp.
Chinese Office Action issued Dec. 31, 2024, in corresponding Chinese Patent Application No. 202080106760.4, 12pp.
Japanese Office Action issued Jan. 28, 2025, in corresponding Japanese Patent Application No. 2022-558820, 11pp.
International Search Report and Written Opinion mailed on Mar. 2, 2021, received for PCT Application PCT/JP2020/045755, filed on Dec. 9, 2020, 8 pages including English Translation.
International Search Report and Written Opinion mailed on Jan. 19, 2021, received for PCT Application PCT/JP2020/045761, filed on Dec. 9, 2020, 10 pages including English Translation.
International Search Report and Written Opinion mailed on Feb. 2, 2021, received for PCT Application PCT/JP2020/045760, filed on Dec. 9, 2020, 9 pages including English Translation.
International Search Report and Written Opinion mailed on Mar. 9, 2021, received for PCT Application PCT/JP2020/045754, filed on Dec. 9, 2020, 9 pages including English Translation.
International Search Report and Written Opinion mailed on Mar. 23, 2021, received for PCT Application PCT/JP2021/003639, filed on Feb. 2, 2021, 8 pages including English Translation.
European Office Action issued Apr. 28, 2025 in European Patent Application No. 21885560.9, 9 pages.
European Office Action issued Jun. 10, 2025 in European Patent Application No. 20959945.5, 7 pages.
European Office Action issued Jun. 27, 2025 in European Patent Application No. 20959942.2, 8 pages.
Chinese Office Action issued Jun. 12, 2025 in Chinese Patent Application No. 202080106760.4, 10 pages.
US Office Action issued Jul. 28, 2025 in related U.S. Appl. No. 18/033,802, 12pp.
US Office Action issued Aug. 14, 2025 in related U.S. Appl. No. 18/033,812, 68pp.
US Office Action issued Jul. 2, 2025 in related U.S. Appl. No. 18/033,815, 66pp.
US Office Action issued Jun. 12, 2025 in related U.S. Appl. No. 18/033,849, 8pp.
Communication pursuant to Article 94(3) EPC issued Jul. 10, 2025 in corresponding European Patent Application No. 20 959 943.0, 7pp.
Chinese Office Action issued Jul. 30, 2025, in corresponding Chinese Patent Application No. 202080106764.2, with Machine Translation by Global Dossier, 10pp.
Japanese Office Action issued Aug. 5, 2025, in corresponding Japanese Patent Application No. 2024-212100, with Machine Translation by Global Dossier, 10pp.
Communication pursuant to Article 94(3) EPC issued Nov. 7, 2025, in corresponding European Patent Application No. 20 959 945.5, 5pp.
Office Action issued Dec. 5, 2025, in corresponding U.S. Appl. No. 18/033,849, 9pp.
Communication pursuant to Article 94(3) EPC issued Dec. 8, 2025, in corresponding European Patent Application No. 20 959 942.2, 10pp.
Office Action issued Dec. 8, 2025, in corresponding U.S. Appl. No. 18/033,802, 14pp.
Communication pursuant to Article 94(3) EPC issued Dec. 12, 2025, in corresponding European Patent Application No. 20 959 943.0, 4pp.
Office Action issued Dec. 16, 2025, in corresponding U.S. Appl. No. 18/033,815, 17pp.
Office Action issued Jan. 20, 2026, in corresponding Japanese Patent Application No. 2024-212100, 12pp.
Office Action (Rejection Decision) issued Feb. 6, 2026 in Chinese Patent Application No. 202080106760.4, 8 pages.
Office Action issued Feb. 11, 2026 in Chinese Patent Application No. 202180073485.5, 16 pages.
Office Action issued Apr. 2, 2026 in U.S. Appl. No. 18/033,815, 20 pages.
Decision of Refusal issued Jun. 23, 2026 in Japanese Patent Application No. 2024-212100, 2 pages.
Decision of Dismissal of Amendment issued Jun. 23, 2026 in Japanese Patent Application No. 2024/212100, 7 pages.

* cited by examiner 10
60
60L
60R
62L
62R
61L
61R
40(40L,40R)
50
50L
50R
51L 52L 53L
51R 52R 53R
top view
side view
30
32
32A
32B
31L,31R
31RA
31RB
20
OL
OR
OS
OL,OR
DM1
Subject's Eye
x
y
z

FIG.3

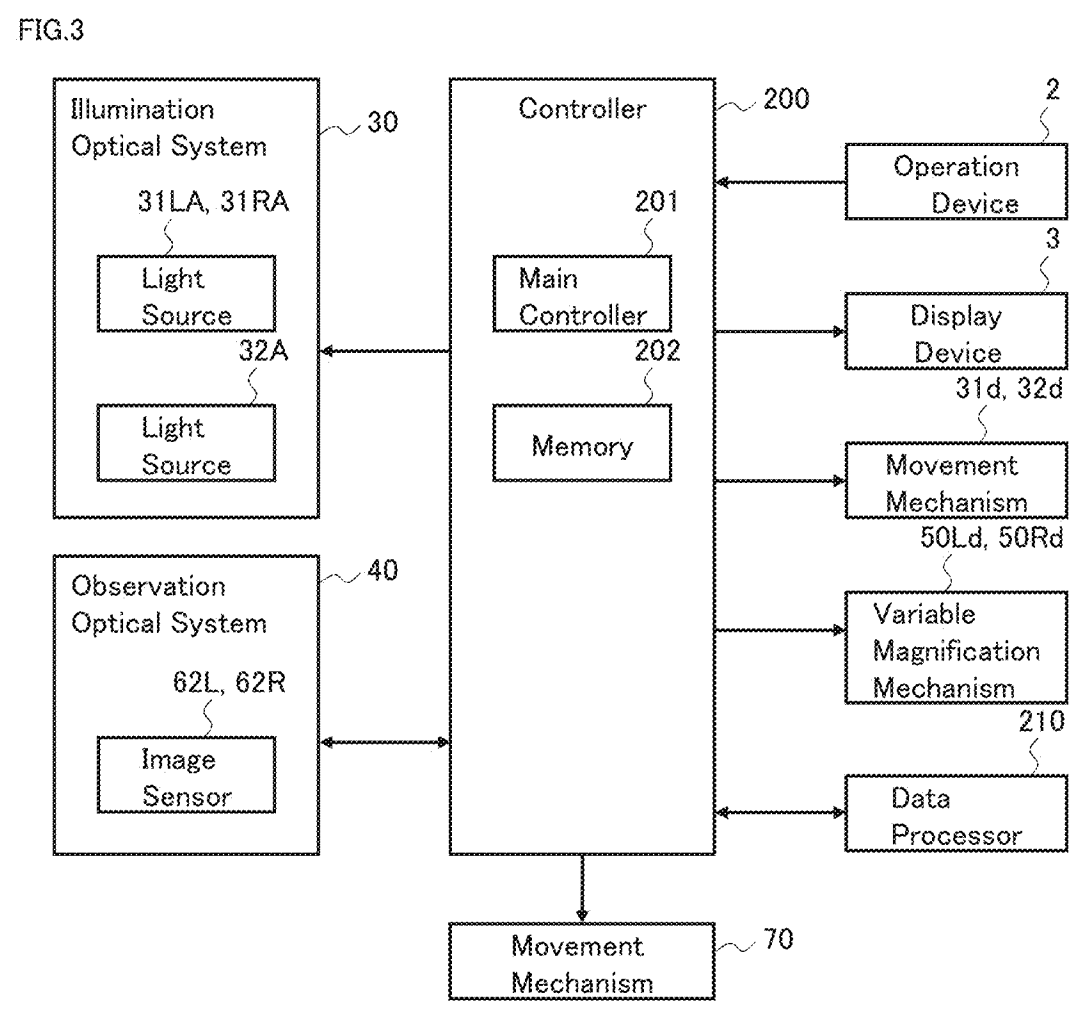

Illumination Optical System 30
Light Source 31LA, 31RA
Light Source 32A
Observation Optical System 40
Image Sensor 62L, 62R
Controller 200
Main Controller 201
Memory 202
Movement Mechanism 70
Operation Device 2
Display Device 3
Movement Mechanism 31d, 32d
Variable Magnification Mechanism 50Ld, 50Rd
Data Processor 210

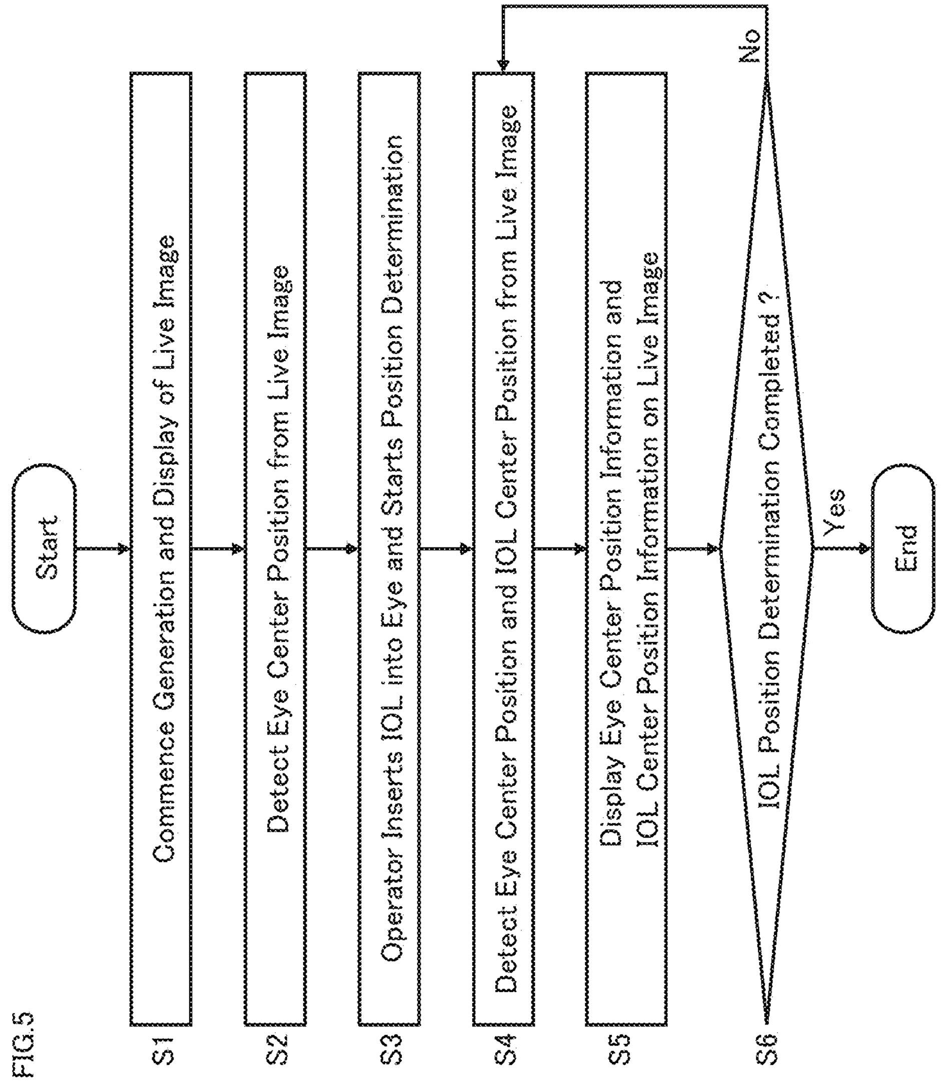
FIG.5
Start
S1
Commence Generation and Display of Live Image
S2
Detect Eye Center Position from Live Image
S3
Operator Inserts IOL into Eye and Starts Position Determination
S4
Detect Eye Center Position and IOL Center Position from Live Image
S5
Display Eye Center Position Information and IOL Center Position Information on Live Image
S6
IOL Position Determination Completed ?
No
Yes
End

OPHTHALMIC OBSERVATION APPARATUS, METHOD OF CONTROLLING THE SAME, AND RECORDING MEDIUM

CROSS-REFERENCE TO RELATED APPLICATIONS

This application is a national stage (under 35 U.S.C. 371) of International Patent Application No. PCT/JP2020/045754, filed Dec. 9, 2020, claiming priority to U.S. Provisional Patent Application Ser. No. 63/106,087, filed Oct. 27, 2020, entitled "APPARATUS AND METHOD FOR OPHTHALMIC OBSERVATION", both of which are herein incorporated by reference in their entirety.

FIELD

The present disclosure relates generally to an ophthalmic observation apparatus, a method of controlling the same, a program, and a recording medium.

At page 1, please amend the heading before paragraph [0003] as follows:

BACKGROUND

An ophthalmic observation apparatus is an apparatus for observing an eye of a patient (which will be referred to as a subject's eye hereinafter). Ophthalmic observation is conducted to grasp the condition of the subject's eye in various situations such as examination, surgery, and treatment.

Conventional ophthalmic observation apparatuses are configured to provide a user with a magnified image formed by an objective lens, a variable magnification optical system, etc. via an eyepiece. In recent years, some ophthalmic observation apparatuses are configured to photograph a magnified image formed by an objective lens, a variable magnification optical system, etc. with an image sensor, and display the photographed image obtained (such an ophthalmic observation apparatus will be referred to as a digital ophthalmic observation apparatus). Examples of such digital ophthalmic observation apparatuses include surgical microscopes, slit lamp microscopes, and fundus cameras (retinal cameras). In addition, various kinds of ophthalmic examination apparatuses such as refractometers, keratometers, tonometers, specular microscopes, wavefront analyzers, and microperimeters are also provided with the function of the digital ophthalmic observation apparatus.

Furthermore, some ophthalmic observation apparatuses of recent years use optical scanning (scanning-type ophthalmic observation apparatus). Examples of such ophthalmic observation apparatuses include scanning laser ophthalmoscopes (SLOs), and optical coherence tomography (OCT) apparatuses.

Generally, an ophthalmic observation apparatus is configured to provide a moving image of a subject's eye to a user (e.g., a health professional (health care practitioner) such as a doctor). A typical digital ophthalmic observation apparatus is configured to perform photographing of a moving image using infrared light and/or visible light as illumination light, and real-time display of the moving image obtained by the moving image photography. On the other hand, a typical scanning-type ophthalmic observation apparatus is configured to perform data collection (data acquisition) by repetitive optical scanning, real-time image reconstruction based on datasets sequentially collected, and real-time moving image display of images sequentially reconstructed. The real-time moving image provided in these ways is referred to as an observation image or a live image.

An ophthalmic observation apparatus capable of providing a real-time moving image is also used in surgery. There are various types of ophthalmic surgery. Some typical surgical methods involve implantation of an artificial object (artificial material, artificial device, artificial instrument, or the like) in the eye. Typical examples of such surgical methods include cataract surgery to replace the crystalline lens with an intraocular lens (IOL), refractive surgery to implant an intraocular contact lens (ICL; also known as a phakic IOL) in the anterior chamber, and minimally invasive glaucoma surgery (MIGS) to place a stent in the trabecular meshwork.

PATENT DOCUMENT 1: Japanese Unexamined Patent Application Publication No. 2019-162336

Surgery to implant an artificial object in the eye requires placing the artificial object in the correct position. For example, in cataract surgery and refractive surgery, lens centering (i.e., an operation of aligning the center of the lens with the axis of the eye) is conducted to avoid problems and inconvenience such as defocusing after surgery. MIGS involves an operation of positioning the stent with respect to the trabecular meshwork to ensure the effectiveness of aqueous humor drainage. Currently, there is no means or method to easily check whether the artificial object is placed at an appropriate position. Therefore, such operations have been laborious and time-consuming. An example of the current situation is that rough positioning or rough alignment for lens centering is performed while referring to the state (condition) of light reflection depicted in the image of the eye provided through an eyepiece or a display device. This is because there is no position indicator available for reference in performing the operation of lens centering.

BRIEF SUMMARY

One object of the present disclosure is to provide a novel method or technique for facilitating ophthalmic observation.

Some aspect examples are an ophthalmic observation apparatus for observing a subject's eye, including: a moving image generating unit configured to generate a moving image by photographing the subject's eye into which an artificial object has been inserted; an analyzing processor configured to analyze a still image included in the moving image to identify a first site image corresponding to a predetermined site of the subject's eye and a second site image corresponding to a predetermined site of the artificial object; and a display controller configured to display, on a display device, the moving image, first position information that represents a position of the first site image, and second position information that represents a position of the second site image.

In the ophthalmic observation apparatus of some aspect examples, the display controller may be configured to display information on the basis of a positional difference between the first site image and the second site image based on the position of the first site image and the position of the second site image.

In the ophthalmic observation apparatus of some aspect examples, the display controller may be configured to display first guide information that represents a movement direction of the artificial object.

In the ophthalmic observation apparatus of some aspect examples, the display controller may be configured to display second guide information that represents a movement distance of the artificial object.

In the ophthalmic observation apparatus of some aspect examples, the display controller may be configured to display the first position information and the second position information in mutually different aspects.

In the ophthalmic observation apparatus of some aspect examples, the analyzing processor may be configured to sequentially identify first site images and second site images from still images sequentially generated by the moving image generating unit, in parallel with generation of the moving image performed by the moving image generating unit, and the display controller may be configured to sequentially update the first position information and the second position information displayed together with the moving image, in parallel with sequential generation of the still images performed by the moving image generating unit and sequential analysis of the still images performed by the analyzing processor.

In the ophthalmic observation apparatus of some aspect examples, the predetermined site of the artificial object may be at least one of an edge of an intraocular lens, an approximate figure to the edge, a center of the intraocular lens, and a hole of the intraocular lens.

In the ophthalmic observation apparatus of some aspect examples, the predetermined site of the subject's eye may be at least one of a corneal ring, an approximate figure to the corneal ring, a corneal center, a pupil edge, an approximate figure to the pupil edge, and a pupil center.

Some aspect examples are a method of controlling an ophthalmic observation apparatus including an optical system for generating a moving image of a subject's eye and a processor, the method including: causing the optical system to generate a moving image of the subject's eye into which an artificial object has been inserted; causing the processor to analyze a still image included in the moving image to identify a first site image corresponding to a predetermined site of the subject's eye and a second site image corresponding to a predetermined site of the artificial object; and causing the processor to display, on a display device, the moving image, first position information that represents a position of the first site image, and second position information that represents a position of the second site image.

Some aspect examples are a program configured to cause a computer to execute the method of some aspect examples.

Some aspect examples are a computer-readable non-transitory recording medium storing the program of some aspect examples.

These aspect examples allow ophthalmic surgery to be facilitated.

BRIEF DESCRIPTION OF THE SEVERAL VIEWS OF THE DRAWING

FIG. 3 is a diagram illustrating an example of a configuration of an ophthalmic observation apparatus according to an embodiment example.

FIG. 5 is a flowchart illustrating an example of processing performed by an ophthalmic observation apparatus according to an embodiment example.

DETAILED DESCRIPTION OF THE INVENTION

Figure 1:
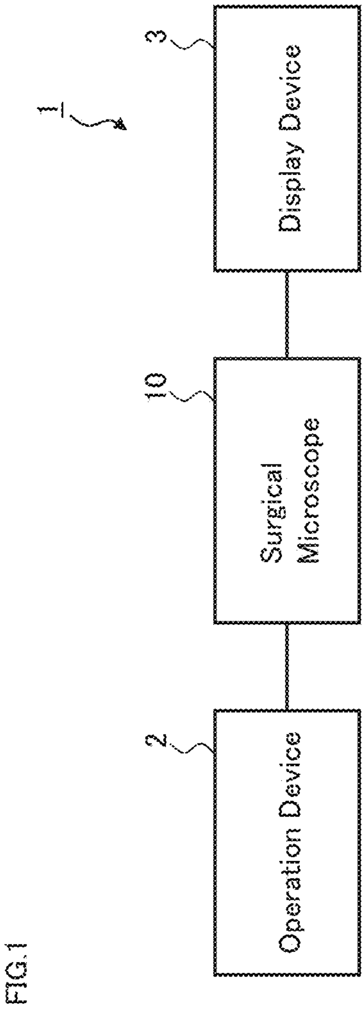
FIG. 1 is a diagram illustrating an example of a configuration of an ophthalmic observation apparatus (ophthalmic surgical microscope) according to an embodiment example.

Some aspect examples of an ophthalmic observation apparatus, a method of controlling the same, a program, and a recording medium according to some embodiments will be described in detail with reference to the drawings. It should be noted that any of the matters and items described in the documents cited in the present disclosure and any known techniques and technologies may be combined with any of the aspect examples.

The ophthalmic observation apparatus according to some aspect examples is used in medical practice (healthcare practice) such as surgery, examination, and treatment, in order to grasp (understand, recognize, find) the state of the subject's eye. The ophthalmic observation apparatus of the aspect examples described herein is mainly a surgical microscope system. However, ophthalmic observation apparatuses of embodiments are not limited to surgical microscope systems. For example, the ophthalmic observation apparatus of some aspect examples may be any of a slit lamp microscope, a fundus camera, a refractometer, a keratometer, a tonometer, a specular microscope, a wavefront analyzer, a microperimeter, an SLO, and an OCT apparatus. Also, the ophthalmic observation apparatus of some aspect examples may be a system that includes any one or more of these apparatus examples. In a wider sense, the ophthalmic observation apparatus of some aspect examples may be any type of ophthalmic apparatus having an observation function.

A target ocular site for observation (ocular site to be observed, ocular site subject to observation) by using the ophthalmic observation apparatus may be any site of the subject's eye, and may be any site of the anterior eye segment and/or any site of the posterior eye segment. Examples of the observation target sites of the anterior eye segment include cornea, iris, anterior chamber, corner angle, crystalline lens, ciliary body, and zonule of Zinn. Examples of the observation target sites of the posterior eye segment include retina, choroid, sclera, and vitreous body. The observation target site is not limited to tissues of an eye ball, and may be any site subject to be observed in ophthalmic medical practice (and/or medical practice in other medical fields) such as eyelid, meibomian gland, and orbit (eye socket, eye pit).

The ophthalmic observation apparatus is used for observing an artificial object inserted into the eye. The artificial object may be a freely selected device (instrument) that is implanted (placed) in the eye. Examples of such an artificial object include an intraocular lens, an intraocular contact lens, and an MIGS device (stent). Note that the artificial objects may be a freely selected medical instrument such as a surgical instrument, an examination instrument, or a treatment instrument.

At least one or more of the functions of the elements described in the present disclosure are implemented by using a circuit configuration (or circuitry) or a processing circuit configuration (or processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), a conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Ophthalmic Observation Apparatus>

FIG. 1 shows the configuration of the ophthalmic observation apparatus of some aspect examples.

The ophthalmic observation apparatus 1 (surgical microscope system, operation microscope system) according to the present embodiment includes the operation device 2, the display device 3, and the surgical microscope (operation microscope) 10. In some aspects, the surgical microscope 10 may include at least one of the operation device 2 and the display device 3. In some aspects, the display device 3 may not be included in the ophthalmic observation apparatus 1. In other words, the display device 3 may be a peripheral device of the ophthalmic observation apparatus 1.

<Operation Device 2>

The operation device 2 includes an operation device and/or an input device. For example, the operation device 2 may include any of a button, a switch, a mouse, a keyboard, a trackball, an operation panel, a dial, and so forth. Typically, the operation device 2 includes a foot switch, like standard (general, normal, usual) ophthalmic surgical microscopes. Further, the operation device 2 may also be configured in such a manner that the user performs operations using voice recognition, line-of-sight (gaze) input, or like input technologies.

<Display Device 3>

The display device 3 displays an image of the subject's eye acquired by the surgical microscope 10. The display device 3 includes a display device such as a flat panel display. The display device 3 may include any of various kinds of display devices such as a touch panel. The display device 3 of some typical aspects includes a display device with a large screen. The display device 3 includes one or more display devices. In the case where the display device 3 includes two or more display devices, for example, one may be a display device with a relatively large screen and one of the other(s) may be a display device with a relatively small screen. Also, a configuration may be employed in which a plurality of display regions is provided in one display device to display a plurality of pieces of information.

The operation device 2 and the display device 3 do not have to be separate devices. For example, a device having both the operation function and the display function, such as a touch panel, may be used as the display device 3. In such a case, the operation device 2 may include a computer program in addition to the touch panel. A content of an operation made by the operation device 2 is sent to a processor (not shown in the drawings) as an electric signal. Further, a graphical user interface (GUI) displayed on the display device 3 and the operation device 2 may be used to conduct operations (instructions) and input information. In some aspects, the functions of the operation device 2 and the display device 3 may be implemented with a touch screen.

<Surgical Microscope 10>

The surgical microscope 10 is used for observation of the eye of a patient (subject's eye) in the supine position. The surgical microscope 10 performs photographing of the subject's eye to generate digital image data. In particular, the surgical microscope 10 generates a moving image of the subject's eye. The moving image (video, movie) generated by the surgical microscope 10 is transmitted to the display device 3 through a wired and/or wireless signal path and displayed on the display device 3. The user (e.g., surgeon) can carry out surgery while observing the subject's eye through the displayed image. In addition to such observation through the displayed image, the surgical microscope 10 of some aspects may also be capable of providing observation through an eyepiece as in conventional technology.

In some aspects, the surgical microscope 10 includes a communication device for transmitting and receiving electrical signals to and from the operation device 2. The operation device 2 receives an operation (instruction) performed by the user and generates an electric signal (operation signal) corresponding to the operation. The operation signal is transmitted to the surgical microscope 10 through a wired and/or wireless signal path. The surgical microscope 10 executes processing corresponding to the operation signal received.

<Optical System of Surgical Microscope 10>

An example of the configuration of the optical system of the surgical microscope 10 will be described. Below, directions are defined as follows, for convenience of description:

the z direction is defined to be the optical axis direction (direction along the optical axis) of the objective lens (the z direction is, for example, the vertical direction, the up and down direction during surgery); the x direction is defined to be a predetermined direction perpendicular to the z direction (the x direction is, for example, the horizontal direction during surgery, and the left and right direction for the surgeon and the patient during surgery); and the y direction is defined to be the direction perpendicular to both the z and x directions (the y direction is, for example, the horizontal direction during surgery, the front and back direction for the surgeon during surgery, and the body axis direction (direction along the body axis) for the patient during surgery).

In addition, the case where the observation optical system includes a pair of left and right optical systems (optical systems capable of binocular observation) will be mainly described below. However, an observation optical system of some other aspects may have an optical system for monocular observation, and it will be understood by those skilled in the art that the configuration described below may be incorporated into the aspects for monocular observation.

Figure 2:
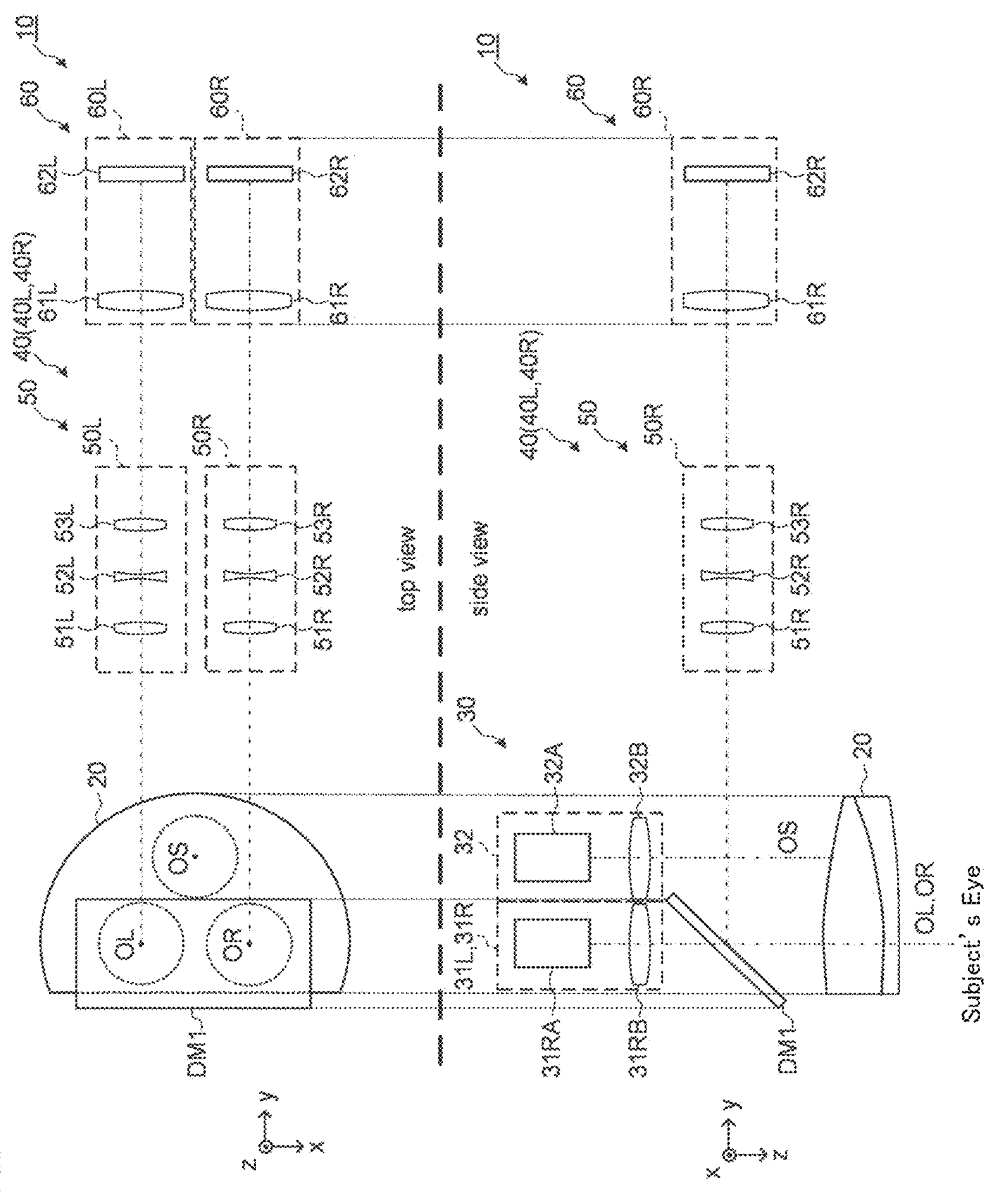
FIG. 2 is a diagram illustrating an example of a configuration of an ophthalmic observation apparatus according to an embodiment example.

FIG. 2 shows an example of the configuration of the optical system of the surgical microscope 10. FIG. 2 illustrates a schematic top view of the optical system viewed from above (top view) and a schematic side view of the optical system viewed from the side (side view) in association with each other. In order to simplify the illustration, the illumination optical system 30 arranged above the objective lens 20 is omitted in the top view.

The surgical microscope 10 includes the objective lens 20, the dichroic mirror DM1, the illumination optical system 30, and the observation optical system 40. The observation optical system 40 includes the zoom expander 50, and the imaging camera 60. In some aspects, the illumination optical system 30 or the observation optical system 40 includes the dichroic mirror DM1.

The objective lens 20 is arranged to face the subject's eye. The objective lens 20 is arranged such that its optical axis is oriented along the z direction. The objective lens 20 may include two or more lenses.

The dichroic mirror DM1 couples the optical path of the illumination optical system 30 and the optical path of the observation optical system 40 with each other. The dichroic mirror DM1 is arranged between the illumination optical system 30 and the objective lens 20. The dichroic mirror DM1 transmits illumination light from the illumination optical system 30 and directs the illumination light to the subject's eye through the objective lens 20. Also, the dichroic mirror DM1 reflects return light from the subject's eye incident through the objective lens 20 and directs the return light to the imaging camera 60 of the observation optical system 40.

The dichroic mirror DM1 coaxially couples the optical path of the illumination optical system 30 and the optical path of the observation optical system 40 with each other. In other words, the optical axis of the illumination optical system 30 and the optical axis of the observation optical system 40 intersect at the dichroic mirror DM1. In the case where the illumination optical system 30 includes an illumination optical system for left eye (31L) and an illumination optical system for right eye (31R) and where the observation optical system 40 includes an observation optical system for left eye 40L and an observation optical system for right eye 40R, the dichroic mirror DM1 coaxially couples the optical path of the illumination optical system for left eye (the first illumination optical system 31L) and the optical path of the observation optical system for left eye 40L with each other, and coaxially couples the optical path of the illumination optical system for right eye (the first illumination optical system 31R) and the optical path of the observation optical system for right eye 40R with each other.

The illumination optical system 30 is an optical system for illuminating the subject's eye through the objective lens 20. The illumination optical system 30 may be configured to selectively illuminate the subject's eye with two or more pieces of illumination light having different color temperatures. The illumination optical system 30 projects illumination light having a designated color temperature onto the subject's eye under the control of a controller (the controller 200 described later).

The illumination optical system 30 includes the first illumination optical systems 31L and 31R and the second illumination optical system 32.

Each of the optical axis OL of the first illumination optical system 31L and the optical axis OR of the first illumination optical system 31R is arranged with the optical axis of the objective lens 20 in a substantially coaxial manner. Such arrangements enable a coaxial illumination mode and therefore make it possible to obtain a red reflex image (transillumination image) formed by utilizing diffuse reflection from eye fundus. The present aspect allows the red reflex image of the subject's eye to be observed with both eyes.

The second illumination optical system 32 is arranged in such a manner that its optical axis OS is eccentric (deviated, shifted) from the optical axis of the objective lens 20. The first illumination optical systems 31L and 31R and the second illumination optical system 32 are arranged such that the deviation of the optical axis OS with respect to the optical axis of the objective lens 20 is larger than the deviations of the optical axes OL and OR with respect to the optical axis of the objective lens 20. Such arrangements enable an illumination mode referred to as "angled illumination (oblique illumination)" and therefore enables binocular observation of the subject's eye while preventing ghosting caused by corneal reflection or the like. In addition, the arrangements enable detailed observation of unevenness and irregularities of sites and tissues of the subject's eye.

The first illumination optical system 31L includes the light source 31LA and the condenser lens 31LB. The light source 31LA outputs illumination light having a wavelength in the visible range (visible region) corresponding to color temperature of 3000 K (kelvins), for example. The illumination light emitted from the light source 31LA passes through the condenser lens 31LB, passes through the dichroic mirror DM1, passes through the objective lens 20, and then is incident on the subject's eye.

The first illumination optical system 31R includes the light source 31RA and the condenser lens 31RB. The light source 31RA also outputs illumination light having a wavelength in the visible range corresponding to color temperature of 3000 K, for example. The illumination light emitted from the light source 31RA passes through the condenser lens 31RB, passes through the dichroic mirror DM1, passes through the objective lens 20, and then is incident on the subject's eye.

The second illumination optical system 32 includes the light source 32A and the condenser lens 32B. The light source 32A outputs illumination light having a wavelength in the visible range corresponding to a color temperature within the range of 4000 K to 6000 K, for example. The illumination light emitted from the light source 32A passes through the condenser lens 32B, passes through the objective lens 20 without passing through the dichroic mirror DM1, and then is incident on the subject's eye.

In the present aspect example, the color temperature of the illumination light from the first illumination optical systems 31L and 31R is lower than the color temperature of the illumination light from the second illumination optical system 32. Such a configuration makes it possible to observe the subject's eye in warm colors using the first illumination optical systems 31L and 31R, and therefore enables detailed observation of the structure and morphology of the subject's eye.

In some aspects, each of the optical axes OL and OR is movable relative to the optical axis of the objective lens 20. The direction of the relative movement is a direction that intersects the optical axis of the objective lens 20, and the relative movement is represented by a displacement vector in which at least one of the x component and the y component is not zero. In some aspects, the optical axes OL and OR may be mutually independently movable. On the other hand, in some aspects, the optical axes OL and OR may be integrally movable. For example, the surgical microscope 10 includes a movement mechanism (31*d*) configured to move the first illumination optical systems 31L and 31R mutually independently or integrally, and therefore the movement mechanism moves the first illumination optical systems 31L and 31R mutually independently or integrally in a direction intersecting the optical axis of the objective lens 20. Such a configuration makes it possible to conduct adjustment of the appearance condition (appearance state) of the subject's eye. In some aspects, the movement mechanism operates under the control of a controller (the controller 200 described later).

In some aspects, the optical axis OS is movable relative to the optical axis of the objective lens 20. The direction of the relative movement is a direction that intersects the optical axis of the objective lens 20, and the relative movement is represented by a displacement vector in which at least one of the x component and the y component is not zero. For example, the surgical microscope 10 includes a movement mechanism (32*d*) configured to move the second illumination optical system 32, and therefore the movement mechanism moves the second illumination optical system 32 in a direction that intersects the optical axis of the objective lens With such a configuration, it becomes possible to conduct adjustment of the appearance condition (appearance state) of unevenness and irregularities of sites and tissues of the subject's eye. In some aspects, the movement mechanism operates under the control of a controller (the controller 200 described later).

As described above, the present aspect is configured such that the illumination optical system 30 is arranged at the position directly above the objective lens 20 (the position in the transmission direction of the dichroic mirror DM1) and the observation optical system 40 is arranged at the position in the reflection direction of the dichroic mirror DM1. For example, the observation optical system 40 may be arranged in such a manner that the angle formed by the optical axis of the observation optical system 40 and the plane perpendicular to the optical axis of the objective lens 20 (the xy plane) belongs to the range between −20 degrees and +20 degrees.

According to the configuration of the present aspect, the observation optical system 40, which typically has a longer optical path length than the illumination optical system 30, is arranged substantially parallel to the xy plane. Hence, the observation optical system 40 of the present aspect does not interfere with the surgeon's field of view while conventional surgical microscopes, whose observation optical system is oriented along the vertical direction in front of the surgeon's eyes, do. Therefore, the surgeon is capable of easily seeing the screen of the display device 3 arranged in front of the surgeon. In other words, the visibility of displayed information (images and videos of the subject's eye, and other various kinds of reference information) during surgery etc. is improved. In addition, since the housing is not placed in front of the surgeon's eyes, it does not give a sense of oppression to the surgeon, thereby reducing the burden on the surgeon.

The observation optical system 40 is an optical system for observation of an image formed based on return light of the illumination light incident from the subject's eye through the objective lens 20. In the present aspect, the observation optical system 40 guides the image to an image sensor of the imaging camera 60.

As described above, the observation optical system 40 includes the observation optical system for left eye 40L and the observation optical system for right eye 40R. The configuration of the observation optical system for left eye 40L and the configuration of the observation optical system for right eye 40R are the same as or similar to one another. In some aspects, the observation optical system for left eye 40L and the observation optical system for right eye 40R may be configured in such a manner that their optical arrangements can be changed independently of each other.

The zoom expander 50 is also referred to as a beam expander, a variable beam expander, or the like. The zoom expander 50 includes the zoom expander for left eye 50L and the zoom expander for right eye 50R. The configuration of the zoom expander for left eye 50L and the configuration of the zoom expander for right eye are the same as or similar to each other. In some aspects, the zoom expander for left eye 50L and the zoom expander for right eye 50R may be configured in such a manner that their optical arrangements can be changed independently of each other.

The zoom expander for left eye 50L includes the plurality of zoom lenses 51L, 52L, and 53L. At least one of the zoom lenses 51L, 52L, and 53L is movable in the direction along the optical axis with a variable magnification mechanism (not shown in the drawings).

Similarly, the zoom expander for right eye 50R includes the plurality of zoom lenses 51R, 52R, and 53R, and at least one of the zoom lenses 51R, 52R, and 53R is movable in the direction along the optical axis with a variable magnification mechanism (not shown in the drawings).

The variable magnification mechanism(s) may be configured to move a zoom lens of the zoom expander for left eye 50L and a zoom lens of the zoom expander for right eye 50R mutually independently or integrally in the directions along the optical axes. As a result of this, the magnification ratio for photographing the subject's eye is changed. In some aspects, the variable magnification mechanism(s) operates under the control of a controller (the controller 200 described later).

The imaging camera 60 is a device that photographs an image formed by the observation optical system 40 and generates digital image data. The imaging camera 60 is typically a digital camera (digital video camera). The imaging camera includes the imaging camera for left eye 60L and the imaging camera for right eye 60R. The configuration of the imaging camera for left eye 60L and the configuration of the imaging camera for right eye 60R are the same as or similar to one another. In some aspects, the imaging camera for left eye 60L and the imaging camera for right eye 60R may be configured such that their optical arrangements can be changed independently of each other.

The imaging camera for left eye 60L includes the imaging lens 61L and the image sensor 62L. The imaging lens 61L forms an image based on the return light that has passed through the zoom expander for left eye 50L, on the imaging surface (light receiving surface) of the image sensor 62L. The image sensor 62L is an area sensor, and may typically be a charge-coupled device (CCD) image sensor or a complementary metal oxide semiconductor (CMOS) image sensor. The image sensor 62L operates under the control of a controller (the controller 200 described later).

The imaging camera for right eye 60R includes the imaging lens 61R and the image sensor 62R. The imaging lens 61R forms an image based on the return light that has passed through the zoom expander for right eye 50R, on the imaging surface (light receiving surface) of the image sensor 62R. The image sensor 62R is an area sensor, and may typically be a CCD image sensor or a CMOS image sensor. The image sensor 62R operates under the control of a controller (the controller 200 described later).

<Processing System>

Figure 4:
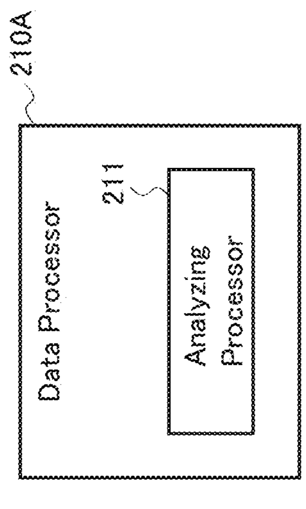
FIG. 4 is a diagram illustrating an example of a configuration of an ophthalmic observation apparatus according to an embodiment example.

The processing system of the ophthalmic observation apparatus 1 will be described. Some configuration examples of the processing system are shown in FIG. 3 and FIG. 4. Any two or more of the various kinds of configuration examples described below may be combined at least in part. Note that the configuration of the processing system is not limited to the examples described below.

The controller 200 executes a control of each part of the ophthalmic observation apparatus 1. The controller 200 includes the main controller 201 and the memory 202. The main controller 201 includes a processor and executes a control of each part of the ophthalmic observation apparatus 1. For example, the processor may load and run a program stored in the memory 202 or another storage device, thereby implementing a function according to the present aspect. In addition, the processor may use (e.g., referring, processing, calculating, etc.) data and/or information stored in the memory 202 or another storage device in order to implement a function according to the present aspect.

The main controller 201 may control the light sources 31LA, 31RA, and 32A of the illumination optical system 30, the image sensors 62L and 62R of the observation optical system 40, the movement mechanisms 31*d* and 32*d*, the variable magnification mechanisms 50Ld and 50Rd, the operation device 2, the display device 3, and other component parts.

Controls of the light source 31LA include turning on and off the light source, adjusting the light amount, adjusting the diaphragm (aperture), and so forth. Controls of the light source 31RA include turning on and off the light source, adjusting the light amount, adjusting the diaphragm (aperture), and so forth. The main controller 201 may perform mutually exclusive controls of the light sources 31LA and 31RA. Controls of the light source 32A include turning on and off the light source, adjusting the light amount, adjusting the diaphragm (aperture), and so forth.

In the case where the illumination optical system 30 includes a light source whose color temperature can be varied, the main controller 201 may change the color temperature of emitted illumination light by controlling such a light source.

Controls of the image sensor 62L include exposure adjustment, gain adjustment, photographing rate adjustment, and so forth. Controls of the image sensor 62R include exposure adjustment, gain adjustment, photographing rate adjustment, and so forth. Further, the main controller 201 may control the image sensors 62L and 62R in such a manner that the photographing timings of the image sensors 62L and 62R match each other, or in such a manner that the difference between the photographing timings of the image sensors 62L and 62R lies within a predetermined time. In addition, the main controller 201 may perform a control of loading digital data obtained by the image sensors 62L and 62R.

The movement mechanism 31*d* moves the light sources 31LA and 31RA mutually independently or integrally in a direction that intersects the optical axis of the objective lens 20. By controlling the movement mechanism 31*d*, the main controller 201 moves the optical axes OL and OR mutually independently or integrally with respect to the optical axis of the objective lens 20.

The movement mechanism 32*d* moves the light source 32A in a direction that intersects the optical axis of the objective lens 20. By controlling the movement mechanism 32*d*, the main controller 201 moves the optical axis OS with respect to the optical axis of the objective lens 20.

The movement mechanism 70 moves the surgical microscope 10. For example, the movement mechanism 70 is configured to integrally move at least part of the illumination optical system 30 and the observation optical system 40. This configuration makes it possible to change the relative positions of the at least part of the illumination optical system 30 and the observation optical system 40 with respect to the subject's eye while maintaining the relative positional relationship between at least part of the illumination optical system 30 and the observation optical system 40. In some aspects, the movement mechanism 70 is configured to integrally move the first illumination optical systems 31L and 31R and the observation optical system 40. With this, the relative positions of the first illumination optical systems 31L and 31R with respect to the subject's eye and the relative position of the observation optical system 40 with respect to the subject's eye can be changed while maintaining the state (condition) of coaxial illumination. In some aspects, the movement mechanism 70 is configured to integrally move the second illumination optical system 32 and the observation optical system 40. With this, the relative positions of the second illumination optical system 32 and the observation optical system 40 with respect to the subject's eye can be changed while maintaining the illumination angle for oblique illumination. In some aspects, the movement mechanism 70 is configured to integrally move the first illumination optical systems 31L and 31R, the second illumination optical system 32, and the observation optical system 40. This makes it possible to change the relative positions of the illumination optical system 30 and the observation optical system 40 with respect to the subject's eye while maintaining both the state (condition) of coaxial illumination and the illumination angle for oblique illumination. The movement mechanism 70 operates under a control of the controller 200.

In some aspects, the main controller 201 may be configured to control at least two of the movement mechanisms 31*d*, 32*d*, and 70 in an interlocking manner.

The variable magnification mechanism 50Ld moves at least one of the plurality of zoom lenses 51L to 53L of the zoom expander for left eye 50L in the optical axis direction (direction along the optical axis). The main controller 201 changes the magnification ratio of the observation optical system for left eye 40L by controlling the variable magnification mechanism 50Ld.

Similarly, the variable magnification mechanism 50Rd moves at least one of the plurality of zoom lenses 51R to 53R of the zoom expander for right eye 50R in the optical axis direction (direction along the optical axis). The main controller 201 changes the magnification ratio of the observation optical system for right eye 40R by controlling the variable magnification mechanism 50Rd.

Controls for the operation device 2 include an operation permission control, an operation prohibition control, an operation signal transmission control and/or an operation signal reception control from the operation device 2, and other controls. The main controller 201 receives an operation signal generated by the operation device 2 and executes a control corresponding to the operation signal received.

Controls for the display device 3 include an information display control and other controls. As a display controller, the main controller 201 displays an image based on digital image data generated by the image sensors 62L and 62R on the display device 3. Typically, the main controller 201 may display a moving image (video, movie) based on digital image data (video signal) generated by the image sensors 62L and 62R on the display device 3. Further, the main controller 201 may display a still image (frame) included in the moving image on the display device 3. In addition, the main controller 201 may display an image (a moving image, a still image, etc.) obtained by processing the digital image data generated by the image sensors 62L and 62R on the display device 3. Furthermore, the main controller 201 may display, on the display device 3, any information generated by the ophthalmic observation apparatus 1, any information acquired from the outside by the ophthalmic observation apparatus 1, and other types of information.

Further, as a display controller, the main controller 201 may create an image for left eye from the digital image data generated by the image sensor 62L and create an image for right eye from the digital image data generated by the image sensor 62R, and then display the created image for left eye and the created image for right eye on the display device 3 in such a manner as to enable stereoscopic vision. For example, the main controller 201 may create a pair of left and right parallax images from the image for left eye and the image for right eye, and display the pair of parallax images on the display device 3. With this, the user (e.g., surgeon) can recognize the pair of parallax images as a stereoscopic image by using a known stereoscopic method or technique. The stereoscopic method applicable to the present aspect may be freely selected, and for example, may be any of the following methods: a stereoscopic method for naked eyes; a stereoscopic method using an auxiliary device (polarized glasses, etc.); a stereoscopic method by applying image processing (image synthesis, image composition, rendering, etc.) to an image for left eye and an image for right eye; a stereoscopic method by displaying a pair of parallax images simultaneously; a stereoscopic method by alternately displaying a pair of parallax images; and a stereoscopic method of a combination of two or more of the above methods.

The data processor 210 executes various kinds of data processes. Some examples of processing that may be executed by the data processor 210 will be described below. The data processor 210 (each element thereof) includes a processor that operates on the basis of predetermined software (program), and is implemented by the cooperation of hardware and software.

Some examples of processing that may be executed by the data processor 210 will be described together with related elements. FIG. 4 shows a configuration example of the data processor 210 (and related elements thereto). The data processor 210A shown in FIG. 4 is an example of the data processor 210 in FIG. 3 and includes the analyzing processor 211.

The surgical microscope 10 is configured to generate a moving image (live image) by photographing the subject's eye into which an artificial object (e.g., an intraocular lens, an intraocular contact lens, an MIGS device, etc.) has been inserted. The controller 200 is configured to capture a moving image frame (still image) and input the captured moving image frame into the analyzing processor 211. In some examples, the controller 200 captures a frame from a moving image in response to a manual or automatic trigger (upon receiving a manual or automatic trigger).

The analyzing processor 211 is configured to analyze the frame captured from the moving image to identify both an image region corresponding to a predetermined site of the subject's eye and an image region corresponding to a predetermined site of the artificial object having been inserted into the subject's eye. In the present disclosure, the image region corresponding to the predetermined site of the subject's eye may sometimes be referred to as the first site image, and the image region corresponding to the predetermined site of the artificial object may sometimes be referred to as the second site image.

The image region corresponding to the predetermined site of the subject's eye may be, for example, an image region identified as an image of the corresponding site, or an image region obtained by applying processing to an image of the corresponding site (and its vicinity). Here, the image region obtained by applying processing to the image of the site (and its vicinity) may be an approximate figure such as an approximate ellipse or an approximate circle. The same applies to the image region corresponding to the predetermined site of the artificial object.

The predetermined site of the subject's eye detected by the analyzing processor 211 may be a freely selected or determined site (part) of the subject's eye. In the case where a target site (a part or region of the subject's eye) to be observed by the ophthalmic observation apparatus 1 is the anterior eye segment, the analyzing processor 211 may be configured to detect any of the following sites, for example: the pupil (its entirety, or a feature site such as the pupil edge, the pupil center, or the pupil center of gravity), the cornea (its entirety, or a feature site such as the corneal ring, the corneal edge, the corneal center, or the corneal apex), the iris (its entirety, or a feature site such as the iris inner edge, the iris outer edge, or the iris pattern), the anterior chamber (its entirety, or a feature site such as the anterior border, or the posterior border), the corner angle (its entirety, a peripheral site, etc.), the crystalline lens (its entirety, or a feature site such as the lens capsule, the anterior capsule, the posterior capsule, or the lens nucleus), the ciliary body, the zonule of Zinn, a blood vessel, and a lesion. In the case where a target site to be observed by the ophthalmic observation apparatus 1 is the posterior eye segment, the analyzing processor 211 may be configured to detect any of the following sites, for example: the optic nerve head, the macula, a blood vessel, the retina (its entirety, the surface, or one or more sub-tissues), the choroid (its entirety, the anterior surface, the posterior surface, or one or more sub-tissues), the sclera (its entirety, the anterior surface, the posterior surface, or one or more sub-tissues), the vitreous body (its entirety, an opaque region, a floating object (floater), a detached tissue, etc.), and a lesion. In the case where a target site to be observed by the ophthalmic observation apparatus 1 is not a tissue of an eye ball, the analyzing processor 211 may be configured to detect a freely selected site or tissue such as the eyelid, the meibomian glands, or the orbit (eye socket, eye pit). The site to be detected by the analyzing processor 211 may be selected or determined depending on an illumination method employed, a site subject to surgery, a surgical method conducted, or other factors.

The analyzing processor 211 may be configured to detect an image of a predetermined site of the subject's eye from a still image using a freely selected region extraction method or technique. In some examples of detecting an image of a site characterized by its brightness (an image of a site that has a distinctive feature in brightness), the analyzing processor 211 may be configured to perform detection of an image of this site of the subject's eye from a still image using brightness thresholding such as binarization. In the case of detecting an image of a site characterized by its shape (an image of a site that has a distinctive feature in shape), the analyzing processor 211 may be configured to perform detection of an image of this site of the subject's eye from a still image using shape analysis processing such as pattern matching. In the case of detecting an image of a site characterized by its color tone (an image of a site that has a distinctive feature in color tone), the analyzing processor 211 may be configured to perform detection of an image of this site of the subject's eye from a still image using color analysis processing such as feature color extraction. In some examples, the analyzing processor 211 may be configured to detect an image of a predetermined site of the subject's eye by applying segmentation to a still image to identify an image of this site of the subject's eye. Typically, segmentation is image processing for identifying a partial region (subregion) in a given image. Segmentation may include any known image processing technique, and some examples of which may include image processing such as edge detection and/or machine learning (e.g., deep learning) based segmentation.

The predetermined site of the artificial object detected by the analyzing processor 211 may be a freely selected or determined site (part) of a freely selected or determined artificial object, and may be, for example, an intraocular lens (its entirety, the optics (lens), the haptics, the outer edge of the optics, the center of the optics, or the hole of the optics), an intraocular contact lens (its entirety, the optics (lens), the haptics, the outer edge of the optics, the center of the optics, the hole of the optics, the outer edge of the haptics, or the hole of the haptics), an MIGS device (its entirety or a part thereof), and so forth. Similar to detection of an image of the predetermined site of the subject's eye, the analyzing processor 211 may detect an image of the predetermined site of the artificial object from a still image using a freely selected or designed region extraction method or technique.

The controller 200 is configured to receive, from the surgical microscope 10, a live image of the subject's eye into which the artificial object has been inserted and display the live image on the display device 3, and also simultaneously (in parallel) display, on the display device 3, the first position information that represents a position of the first site image detected by the analyzing processor 211 and the second position information that represents a position of the second site image detected also by the analyzing processor 211. Here, the position of the first site image is the position of the predetermined site of the subject's eye, and the position of the second site image is the position of the predetermined site of the artificial object.

According to the ophthalmic observation apparatus 1 configured as described above, the position of the predetermined site of the subject's eye and the position of the predetermined site of the artificial object can be provided together with the live image. This enables the user to know the positional relationship between the predetermined site of the subject's eye and the predetermined site of the artificial object in real time. This, as a result, allows the user to easily perform the operation of placing the artificial object in the correct position during surgery to implant the artificial object in the eye, and also to easily confirm whether the artificial object is placed in the proper position, for example. Therefore, according to the ophthalmic observation apparatus 1, it becomes possible to facilitate ophthalmic surgery.

The controller 200 may be configured to display, in mutually different modes or aspects, the first position information that represents the position of the predetermined site of the subject's eye and the second position information that represents the position of the predetermined site of the artificial object. A display mode of the first position information and a display mode of the second position information are different, for example, in at least one item (feature) from among colors, patterns, shapes, and sizes. As a result of this, the user can easily see the position of the predetermined site of the subject's eye and the position of the predetermined site of the artificial object, and also easily recognize the positional relationship between the predetermined site of the subject's eye and the predetermined site of the artificial object.

Either one of or both the display mode of the first position information and the display mode of the second position information may be changed automatically or manually. For example, the data processor 210A is configured to find a positional relationship (e.g., distance, direction, etc.) between the predetermined site of the subject's eye and the predetermined site of the artificial object based on the first site image and the second site image detected by the analyzing processor 211. In addition, the controller 200 is configured to change the display mode of the first position information and/or the display mode of the second position information based on the positional relationship between the predetermined site of the subject's eye and the predetermined site of the artificial object obtained by the data processor 210A. This allows the user to easily (intuitively) understand the positional relationship between the predetermined site of the subject's eye and the predetermined site of the artificial object.

The controller 200 may be configured to display information on the basis of a positional difference between the first site image and the second site image based on the position of the first site image and the position of the second site image detected by the analyzing processor 211, along with the live image generated by the surgical microscope 10. Note that the controller 200 may be configured to display the information on the basis of the positional difference between the first site image and the second site image, together with a live image, and with at least one of the first position information that represents the position of the predetermined site of the subject's eye and the second position information that represents the position of the predetermined site of the artificial object.

The information on the basis of the positional difference between the first site image and the second site image may include, for example, any of the following kinds of information: information that represents a positional difference of the artificial object with respect to the subject's eye; information that represents a positional difference of the actual position of the artificial object with respect to the position where the artificial object should be placed; information that represents a movement direction of the artificial object (a direction in which the artificial object should be moved); information that represents a movement distance of the artificial object (a distance (amount) by which the artificial object should be moved); information that represents a rotation direction of the artificial object (a direction in which the artificial object should be rotated); and information that represents a rotation angle of the artificial object (an angle (amount) by which the artificial object should be rotated). As can be seen from these examples, the information on the basis of the positional difference between the first site image and the second site image may be any of the following kinds of information: information representing a positional difference; information for eliminating or canceling out the positional difference (e.g., guidance or guide information for users); and other kinds of information. The information on the basis of the positional difference between the first site image and the second site image may be in any form, and may be, for example, an image, a figure, a character string, or other forms.

The ophthalmic observation apparatus 1 may be configured to update the first position information and the second position information displayed together with the live image generated by the surgical microscope 10 in real time. Here, the first position information is information that represents the position of the predetermined site of the subject's eye, and the second position information is information that represents the position of the predetermined site of the artificial object. In order to implement this update function, the analyzing processor 211 may be configured to sequentially identify images of the predetermined site of the subject's eye (first site images) and images of the predetermined site of the artificial object (second site images) from frames (still images) sequentially generated by the surgical microscope 10, in parallel with generation of the moving image performed by the ophthalmic surgical microscope 10. In addition, the controller 200 may be configured to sequentially update the first position information and the second position information displayed together with the live image, in parallel with the sequential generation of the still images performed by the surgical microscope 10 and the sequential analysis of the still images performed by the analyzing processor 211. Updating of the first position information is performed based on the first site images sequentially obtained from the live image (the first site images are time-series images). Similarly, updating of the second position information is performed based on the second site images sequentially obtained from the live image (the second site images are time-series images). According to this configuration, the user can become aware, in real time, of changes such as a change in the position of the predetermined site of the subject's eye, a change in the position of the predetermined site of the artificial object, and a change in the positional relationship between the predetermined site of the subject's eye and the predetermined site of the artificial object.

<Operation and Usage Mode>

The operation and the usage mode of the ophthalmic observation apparatus 1 will be described. FIG. 5 shows an example of the operation and the usage mode of the ophthalmic observation apparatus 1. While the present example describes an application to centering operation (that is, an operation or a task for aligning the center of the intraocular lens with the center of the eye) conducted in intraocular lens implantation surgery, substantially the same or a similar operation and substantially the same or a similar usage mode as those in the present example can be implemented also in the cases of applying to other kinds of surgery or to other kinds of artificial objects, except for differences in the surgery or the artificial object to be applied.

(S1: Commence Generation and Display of Live Image)

Figure 6A:
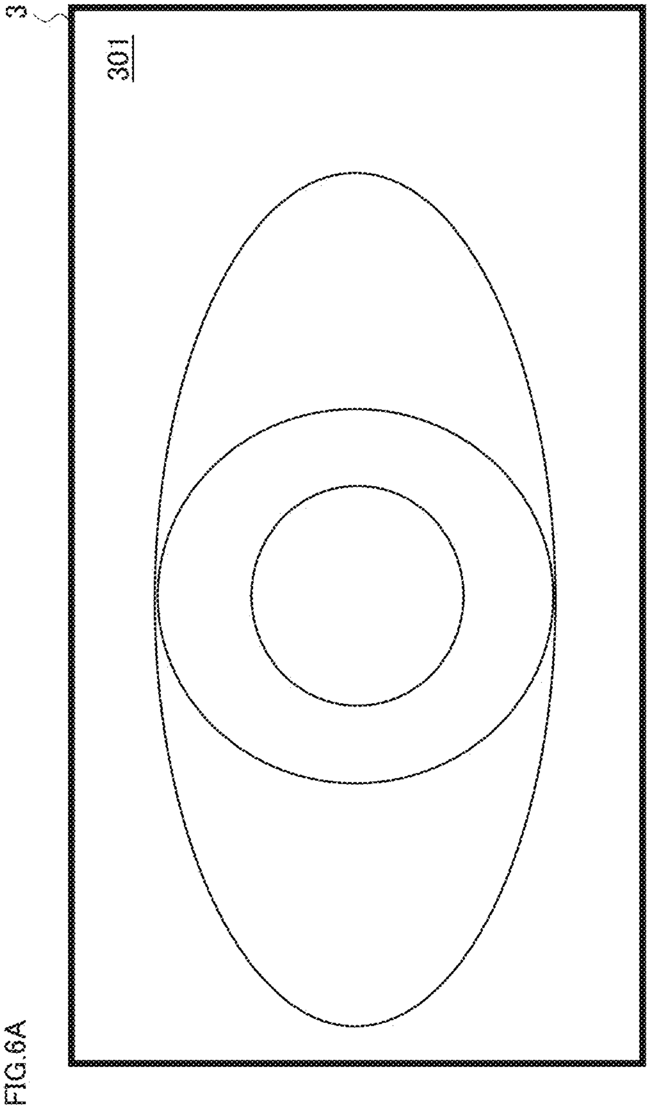
FIG. 6A is a diagram for describing an example of processing performed by an ophthalmic observation apparatus according to an embodiment example.

To begin with, the user performs a predetermined operation using the operation device 2 to cause the ophthalmic observation apparatus 1 to start generating and displaying a live image of the subject's eye (the anterior eye segment thereof). More specifically, the surgical microscope 10 illuminates the subject's eye by the illumination optical system 30, and at the same time (in parallel, simultaneously) generates digital image data (moving image, video) of the subject's eye by the image sensors 62L and 62R. The generated moving image (the live image 301) is displayed in real time on the display device 3 (see FIG. 6A). In other words, a moving image acquired by the surgical microscope 10 is displayed on the display device 3 as a live image (as an observation image). The user can conduct surgery while observing the live image.

(S2: Detect Eye Center Position from Live Image)

Next, the analyzing processor 211 detects a center position of the eye (eye center position) from the live image (from a frame(s) thereof) whose generation has started in the step S1. The eye center position is a position defined in advance as the center position of the subject's eye, and may typically be the corneal center or the pupil center.

Figure 6B:
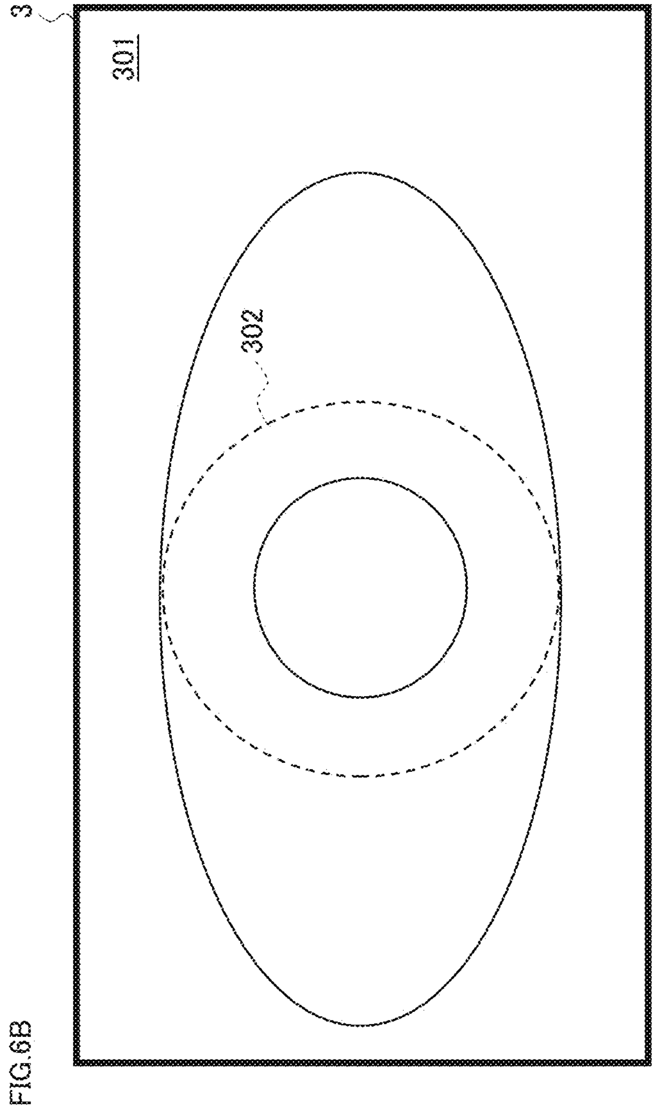
FIG. 6B is a diagram for describing an example of processing performed by an ophthalmic observation apparatus according to an embodiment example.
Figure 6C:
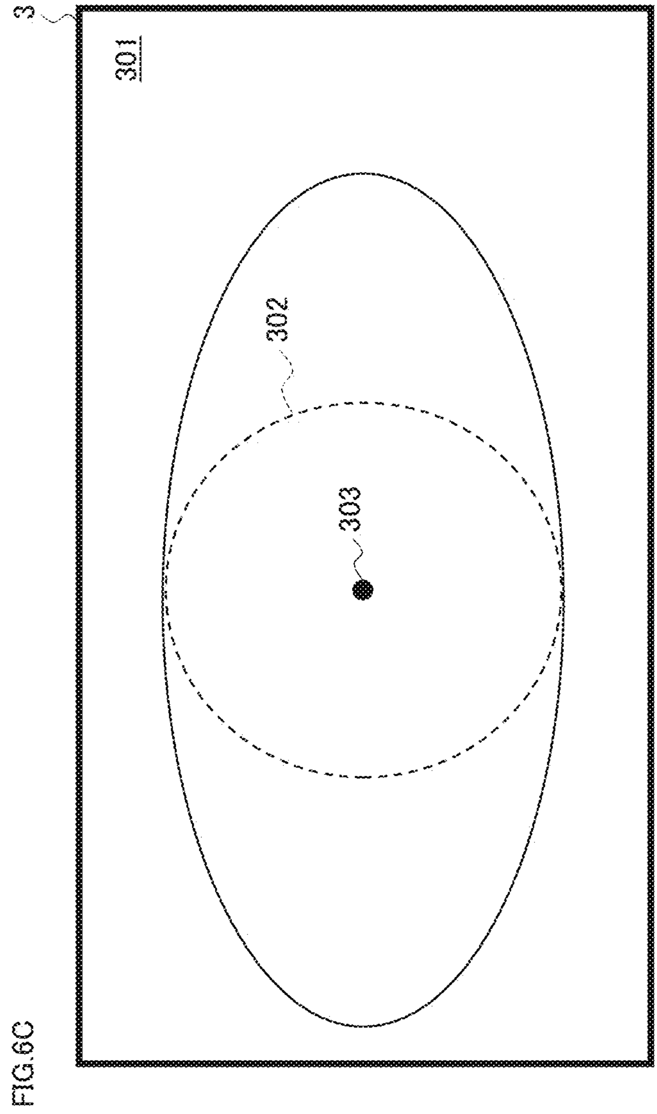
FIG. 6C is a diagram for describing an example of processing performed by an ophthalmic observation apparatus according to an embodiment example.

In order to detect the corneal center, in some aspects, the analyzing processor 211 first applies image processing, such as binarization, edge detection, segmentation, or other methods, to a frame of the live image 301 to detect the corneal ring 302 (see FIG. 6B). Next, the analyzing processor 211 identifies the position (pixel) 303 corresponding to the corneal center based on the corneal ring 302 detected (see FIG. 6C). For example, the analyzing processor 211 finds an approximate ellipse (approximate circle) to the corneal ring 302 detected, and then identifies the center of this approximate ellipse as the corneal center 303. The process of identifying the center of the approximate ellipse is performed, for example, by means of known geometrical techniques.

Figure 6D:
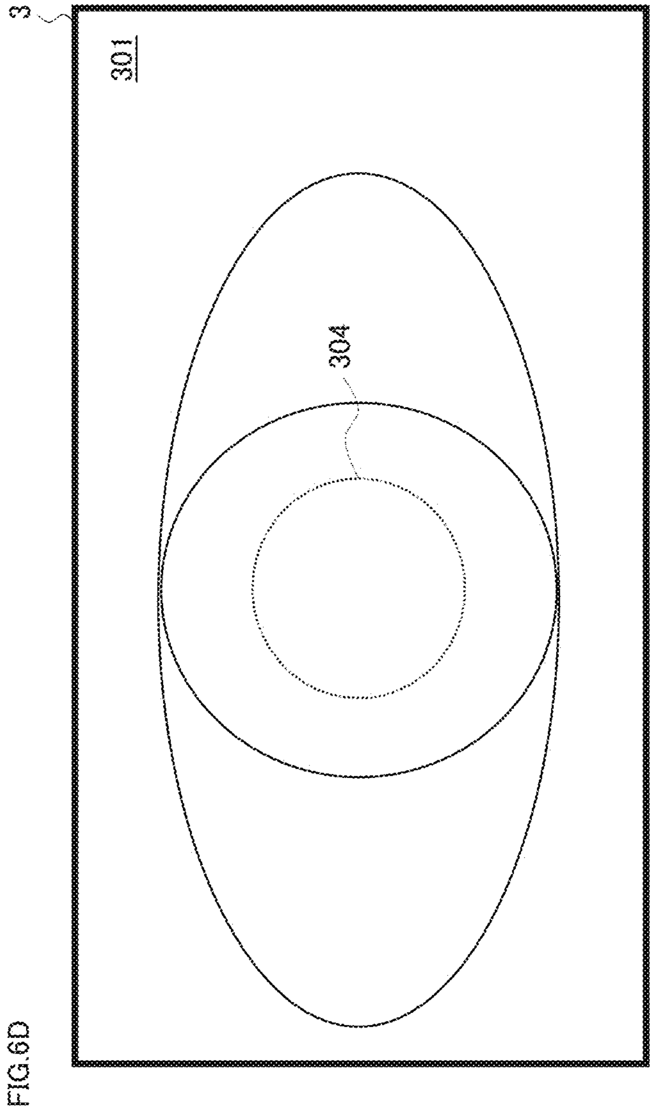
FIG. 6D is a diagram for describing an example of processing performed by an ophthalmic observation apparatus according to an embodiment example.
Figure 6E:
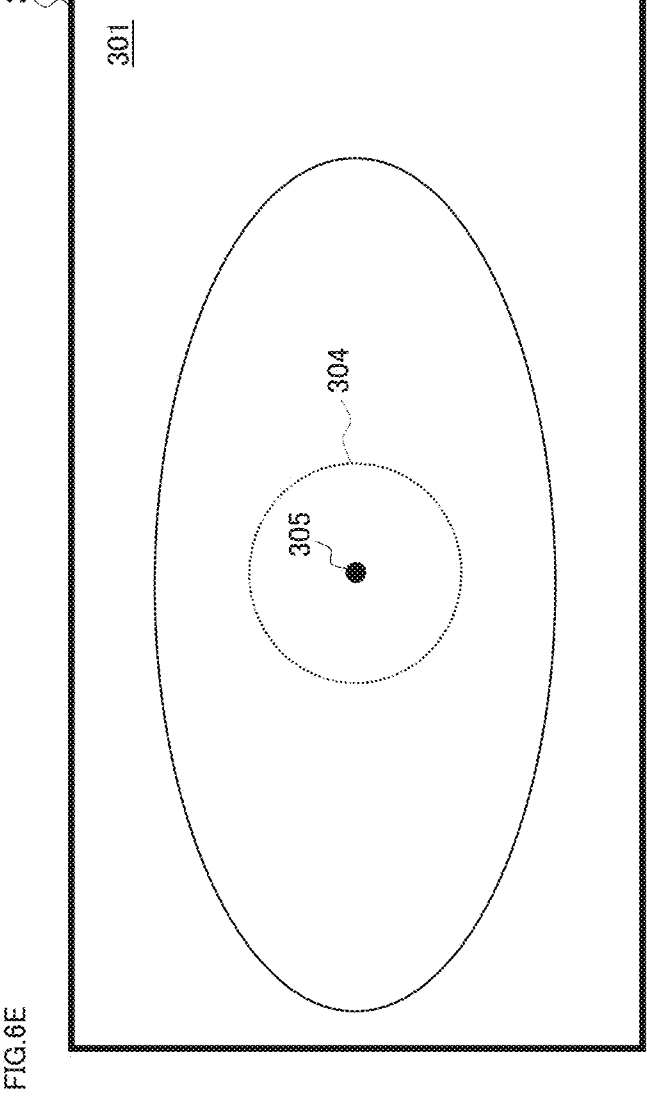
FIG. 6E is a diagram for describing an example of processing performed by an ophthalmic observation apparatus according to an embodiment example.

In order to detect the pupil center, in some aspects, the analyzing processor 211 first applies image processing, such as binarization, edge detection, segmentation, or other methods, to a frame of the live image 301 to detect the pupil edge 304 (see FIG. 6D). Next, the analyzing processor 211 identifies the position (pixel) 305 corresponding to the pupil center based on the pupil edge 304 detected (see FIG. 6E). For example, the analyzing processor 211 finds an approximate ellipse (approximate circle) to the pupil edge 304 detected, and then identifies the center of this approximate ellipse as the pupil center 305. The process of identifying the center of this approximate ellipse is performed, for example, by means of known geometrical techniques.

The processing of the step S2 may be applied to the frames that are sequentially acquired as the live image 301. For example, the processing of the step S2 may be applied to individual frames acquired as the live image 301 (time-series images). Alternatively, the processing of the step S2 may be applied to one or more frames selected from all the frames acquired as the live image 301. The process of selecting frames may include, for example, thinning of selecting frames at intervals of a predetermined number of frames.

The controller 200 may display information that represents the eye center position detected in the step S2 (referred to as eye center position information) on the live image 301. In the case where the processing of the step S2 is applied to the frames sequentially acquired as the live image 301, the controller 200 may update the display of the eye center position information (the displayed eye center position information) each time a new eye center position is detected. This enables the surgeon to know the eye center position of the subject's eye in real time.

(S3: Operator Inserts IOL into Eye and Starts Position Determination)

Next, the surgeon (operator) inserts the intraocular lens into the subject's eye and then starts the process of determining the position in which the intraocular lens is placed (fixed) in conformity with the procedures and techniques of typical cataract surgery (crystalline lens replacement surgery). Here, the position determination process is referred to as positioning, centering, or the like.

(S4: Detect Eye Center Position and IOL Center Position from Live Image)

Figure 6F:
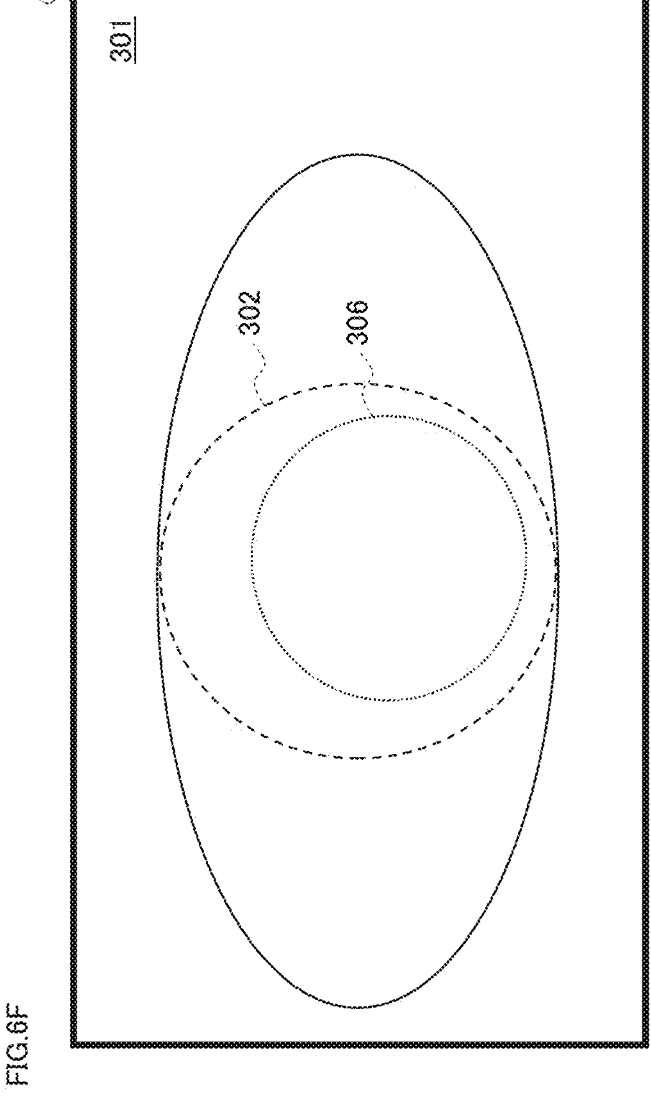
FIG. 6F is a diagram for describing an example of processing performed by an ophthalmic observation apparatus according to an embodiment example.
Figure 6G:
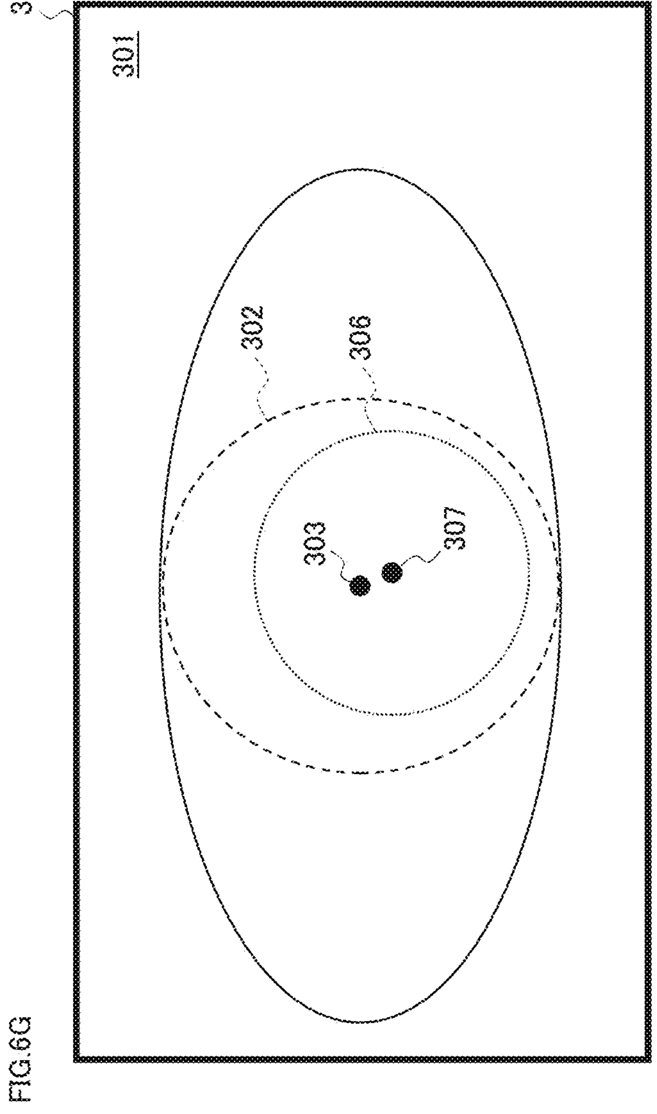
FIG. 6G is a diagram for describing an example of processing performed by an ophthalmic observation apparatus according to an embodiment example.

After the intraocular lens is inserted into the subject's eye in the step S3, the analyzing processor 211 detects an eye center position and an intraocular lens center position from a frame of the live image 301. Detection of the eye center position may be executed in the same or a similar manner as or to the processing in the step S2. The present example describes a case of performing detection of the corneal ring 302 and detection of the corneal center 303 (see FIG. 6F and FIG. 6G).

Detection of the intraocular lens center position may also be executed in the same or a similar manner. For example, the analyzing processor 211 first applies image processing, such as binarization, edge detection, segmentation, or other methods, to a frame of the live image 301 to detect the outer edge 306 of the optics (lens) of the intraocular lens (see FIG. 6F). Next, the analyzing processor 211 identifies the position (pixel) 307 corresponding to the center of the optics of the intraocular lens based on the outer edge 306 detected (see FIG. 6G). For example, the analyzing processor 211 finds an approximate ellipse (approximate circle) to the outer edge 306 detected and then identifies the center of this approximate ellipse as the intraocular lens center position 307. The process of identifying the center of this approximate ellipse is performed, for example, by means of known geometrical methods.

As in the case of the step S2, the processing of the step S4 can be applied to the frames that are sequentially acquired as the live image 301. For example, an eye center position and an intraocular lens center position can be detected by applying the processing of the step S4 to all the frames acquired as the live image 301 (time-series images). Alternatively, an eye center position and an intraocular lens center position can be detected by applying the processing of the step S4 to one or more frames selected from all the frames acquired as the live image 301. The process of selecting frames may include, for example, thinning of selecting frames at intervals of a predetermined number of frames.

(S5: Display Eye Center Position Information and IOL Center Position Information on Live Image)

Next, based on the eye center position and the intraocular lens center position detected in the step S4, the controller 200 displays information that represents the eye center position (referred to as eye center position information) and information that represents the intraocular lens center position (referred to as intraocular lens center position information) on the live image.

Figure 6H:
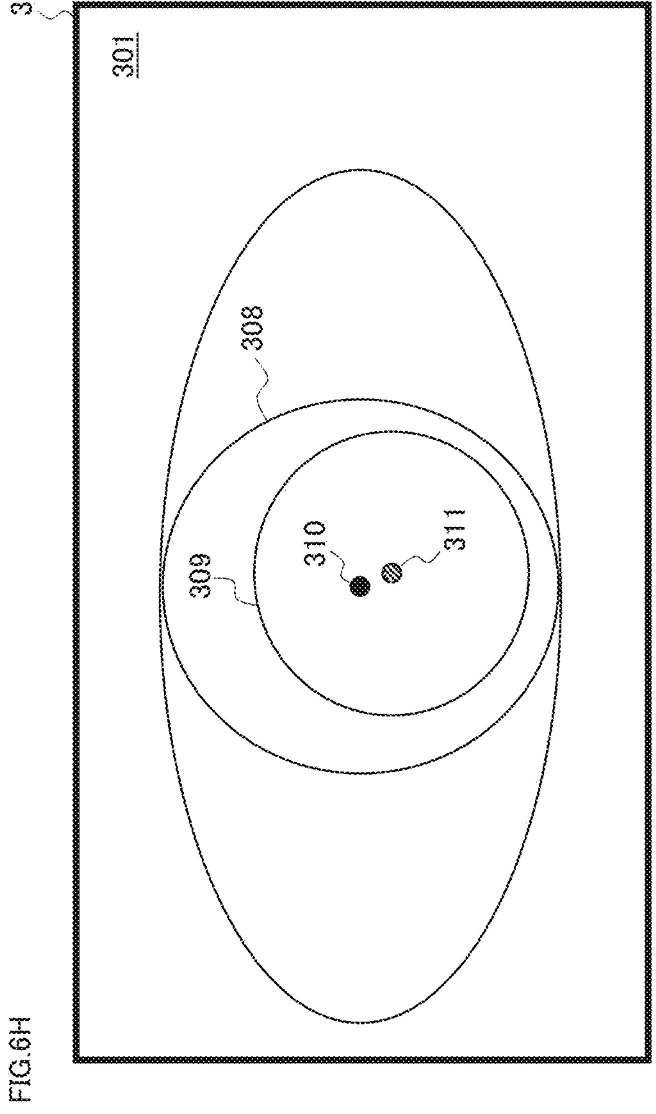
FIG. 6H is a diagram for describing an example of processing performed by an ophthalmic observation apparatus according to an embodiment example.

FIG. 6H shows an example of the mode of the display in the step S5. In the live image 301, the cornea 308 of the subject's eye, the pupil (not shown), the intraocular lens 309 inserted in the step S3, and so forth are depicted. The eye center position information 310 that represents the eye center position detected from the live image 301 in the step S4 and the intraocular lens center position information 311 that represents the intraocular lens center position also detected from the live image 301 in the step S4 are displayed on the live image 301 of the present example. In the present example, the eye center position information 310 and the intraocular lens center position information 311 are displayed in mutually different aspects (mutually different visual aspects, mutually different appearances, mutually different ways or manners). As a result of this, the user can easily recognize both the eye center position and the intraocular lens center position, and can also easily understand the positional relationship (relative position) between the eye center position and the intraocular lens center position. Such a display mode contributes to simplification and facilitation of the intraocular lens positioning.

Figure 6I:
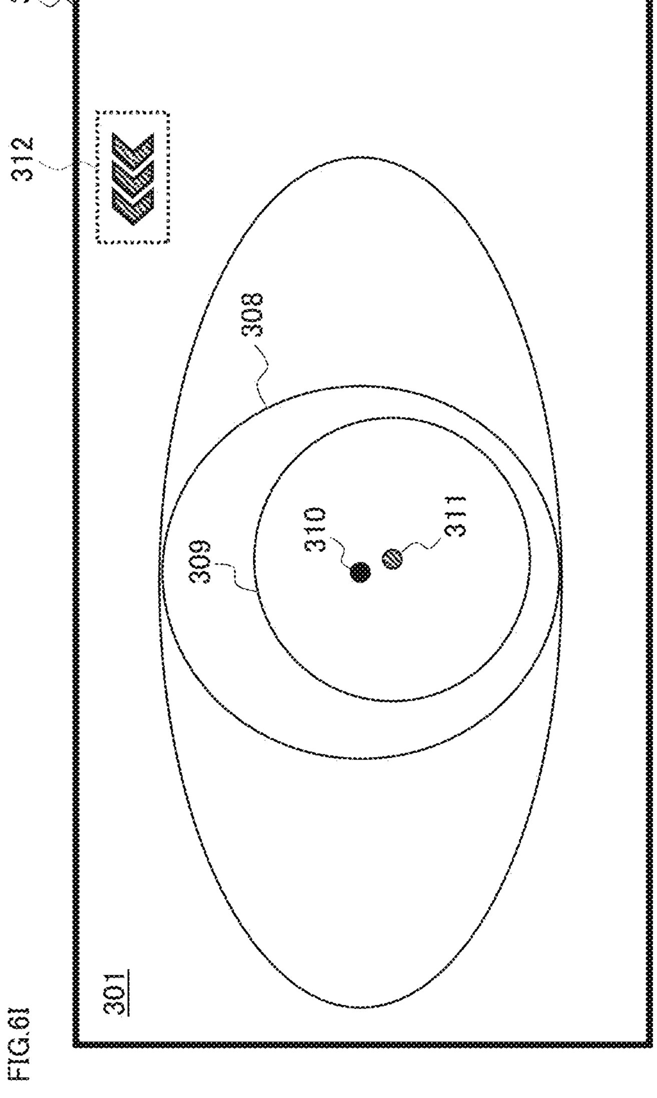
FIG. 6I is a diagram for describing an example of processing performed by an ophthalmic observation apparatus according to an embodiment example.

FIG. 6I shows another example of the mode of the display in the step S5. In the live image 301 of the present example, as in the case of FIG. 6H, the cornea 308 of the subject's eye, the pupil (not shown), the intraocular lens 309 inserted in the step S3, and so forth are displayed. Further, the eye center position information 310 and the intraocular lens center position information 311 are displayed on the live image 301. In addition, in the present example, the controller 200 displays the guide information 312 for eliminating or canceling out the positional difference.

The guide information 312 includes a group of arrow-shaped images that indicates a direction in which the intraocular lens 309 should be moved. The guide information 312 of the present example includes the three arrow-shaped images each pointing to the left. The direction indicated by the arrow-shaped images represents a direction in which the intraocular lens 309 should be moved, that is, the movement direction of the intraocular lens 309 in order to eliminate or cancel out the misalignment (displacement, deviation) of the intraocular lens 309 with respect to the subject's eye. Note that another guide information may be displayed that represents a direction of misalignment of the intraocular lens 309 with respect to the subject's eye. In the present example, the number of arrow-shaped images indicates a distance by which the intraocular lens 309 should be moved, that is, the amount or distance of the misalignment of the intraocular lens 309 with respect to the subject's eye. For example, the amount of misalignment corresponding to one arrow-shaped image is determined in advance.

According to the guide information 312 of the present example, the user can understand the fact that the intraocular lens 309 is misaligned to the right with respect to the subject's eye and also the fact that the intraocular lens 309 should be moved to the left by a distance corresponding to the number of the displayed arrow-shaped images which is three.

The guide information 312 of the present example is generated based on the eye center position and the intraocular lens center position acquired in the step S4. For example, the direction of the group of arrow-shaped images in the guide information 312 is determined as the direction of the vector whose initial point is located at the intraocular lens center position and whose terminal point is located at the eye center position, and the number of arrow-shaped images is determined based on the magnitude (length) of this vector. In this way, the guide information 312 represents the movement direction and the movement amount of the intraocular lens 309 in order to align the intraocular lens center position with the eye center position (in order to match these positions), that is, the movement direction and the movement amount of the intraocular lens 309 to achieve centering of the intraocular lens 309.

In the case where the guide information 312 is being displayed, the user can conduct the centering operation of the intraocular lens 309 by referring to the guide information 312 displayed. In the case where the eye center position information 310 and the intraocular lens center position information 311 are being displayed, the user can conduct the centering operation of the intraocular lens 309 by referring to these pieces of information displayed.

(S6: IOL Position Determination Completed?)

The steps S4 and S5, as well as the centering operation of the intraocular lens 309 by the user (surgeon, operator) are repeated and continued until the position determination (positioning) of the intraocular lens 309 is completed (S6: No). The steps S4 and S5 are performed at predetermined time intervals. With this, the user can perform the positioning operation (centering operation) of the intraocular lens 309 while referring to the eye center position information 310 and the intraocular lens center position information 311 that represent the positional relationship between the subject's eye and the intraocular lens 309 in real time. In addition to or in place of this, the user can perform the positioning operation of the intraocular lens 309 while referring to the guide information 312 that represents the direction to which the intraocular lens 309 should be moved and the distance by which the intraocular lens 309 should be moved.

When the positioning of the intraocular lens 309 is completed (S6: Yes), the detection of the eye center position and the intraocular lens center position, the display of the eye center position information 310 and the intraocular lens center position information 311, and the display of the guide information 312 may be ended (End). Then, the user can move on to the next step of cataract surgery.

Modification Examples

The above embodiment examples have described in particular detail the cases of assisting the user in the centering operation of the intraocular lens by presenting the eye center position information and the intraocular lens center position information on the live image. From the above embodiment examples, those skilled in the art will understand that the same or a similar assistance can be provided in the positioning operation of any kind of intraocular implantable instrument, such as an intraocular contact lens or an MIGS device.

Since implantation of an intraocular contact lens changes the flow state of fluid (aqueous humor) in the eye and increases intraocular pressure, iridotomy for lowering the intraocular pressure has been applied in conventional operation techniques. On the other hand, an intraocular contact lens that has a hole formed in the center of the lens has recently been developed. Such an intraocular contact lens is referred to as a hole ICL. The hole ICL allows aqueous humor to move through the hole, thereby eliminating the need for iridotomy. The hole is very small and has no effect on vision. Note that hole ICLs are not suitable for eyes with certain refractive powers (e.g., farsighted eyes).

In the case of performing implantation surgery of a hole ICL, the ophthalmic observation apparatus 1 may detect the hole formed in the center by the analyzing processor 211, and then display information that represents the position of the detected hole together with a live image by the controller 200. This makes it possible to obtain the same or similar effects as those of the above-described embodiment examples. It should be noted that when the visibility of the hole of the hole ICL depicted in the live image is sufficiently high, the detection of the hole and the display of the position information of the hole may be unnecessary. In such a case, the user can perform positioning (centering) of the intraocular contact lens by referring to the image of the hole itself depicted in the live image and the eye center position information.

A hole ICL is an example of an artificial object that has a feature point (e.g., a hole). The position of the feature point of such an artificial object is designed with high accuracy (high precision) in advance. Therefore, the positional relationship between the feature point and the center of the optics (lens) is known. Note that there are cases where the feature point and the center of the optics do or do not match each other. In the case where the positional relationship is known, the position information of the feature point of the artificial object may be stored in advance in the controller 200 (in the memory 202), the position of the center of the optics (or another site of the optics) of the artificial object may be calculated by referring to the stored position information, and information that represents the calculated position may be displayed together with a live image.

In a wider sense, information on an artificial object to be implanted may be registered in advance, and information that represents the center position of the optics (or a predetermined site of the optics) may be displayed together with a live image. Here, the information on the artificial object may include any of the following kinds of information, for example: position information of a feature part of the artificial object (e.g., hole, mark, character string, unevenness, pattern, etc.); shape information of the whole or part of the artificial object; thickness distribution information of the whole or part of the artificial object; color information of the whole or part of the artificial object; and information of other kinds. Display of the position information of a predetermined site of the artificial object may be started, for example, in response to commencement of depiction of an image of the artificial object within the pupil region of the live image.

In the above embodiment examples, the eye center position is identified based on the corneal ring of the subject's eye, but the method of identifying an eye center position is not limited to this. Even in the case where an eye center position is identified by means of another method, it is possible to present the same or similar guide information as or to any of those of the above embodiment examples. Examples of other methods for identifying an eye center position include a method based on a site of an eye other than the corneal ring (e.g., pupil, iris), a method based on projected light, a method based on an instrument or a mark (sign) placed on or attached to the eye, and a method based on information obtained from other systems (e.g., augmented reality system, virtual reality system).

In the above embodiment examples, the positional relationship between the subject's eye and the lens is determined based on the positional relationship between the center of the eye and the center of the lens; however, the method for determining the positional relationship between the subject's eye and the lens is not limited to this. For example, the positional relationship between the subject's eye and the lens may be determined based on the positional relationship between the corneal ring (or, the pupil edge, the iris inner edge, the iris outer edge) and the lens edge (the outer edge of the lens). In some examples, the positional relationship between the subject's eye and the lens can be determined based on a distance distribution between the corneal ring (or, the pupil edge, the iris inner edge, the iris outer edge) and the lens edge (the outer edge) by utilizing the fact that the corneal ring (or, the pupil edge, the iris inner edge, the iris outer edge) and the lens edge (the outer edge) are both of substantially circular shapes or substantially elliptic shapes. In some alternative examples, the positional relationship between the subject's eye and the lens can be determined based on a distance distribution between an approximate figure to the corneal ring (or, the pupil edge, the iris inner edge, the iris outer edge) and an approximate figure to the lens edge (the outer edge).

Figure 7A:
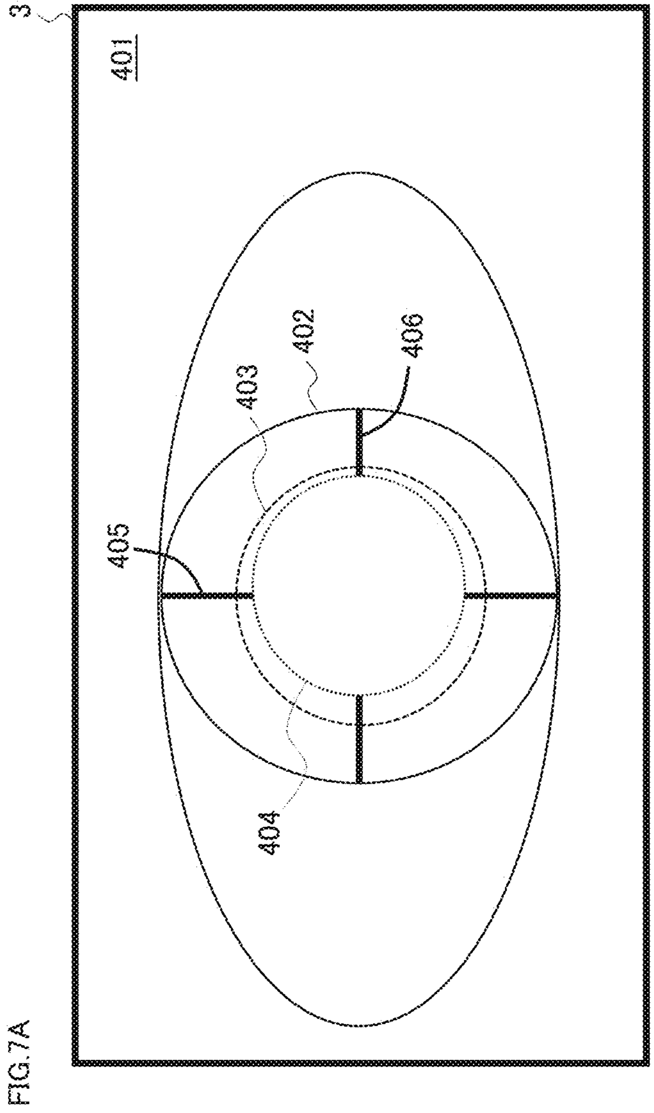
FIG. 7A is a diagram for describing an example of processing performed by an ophthalmic observation apparatus according to a modification example.
Figure 7B:
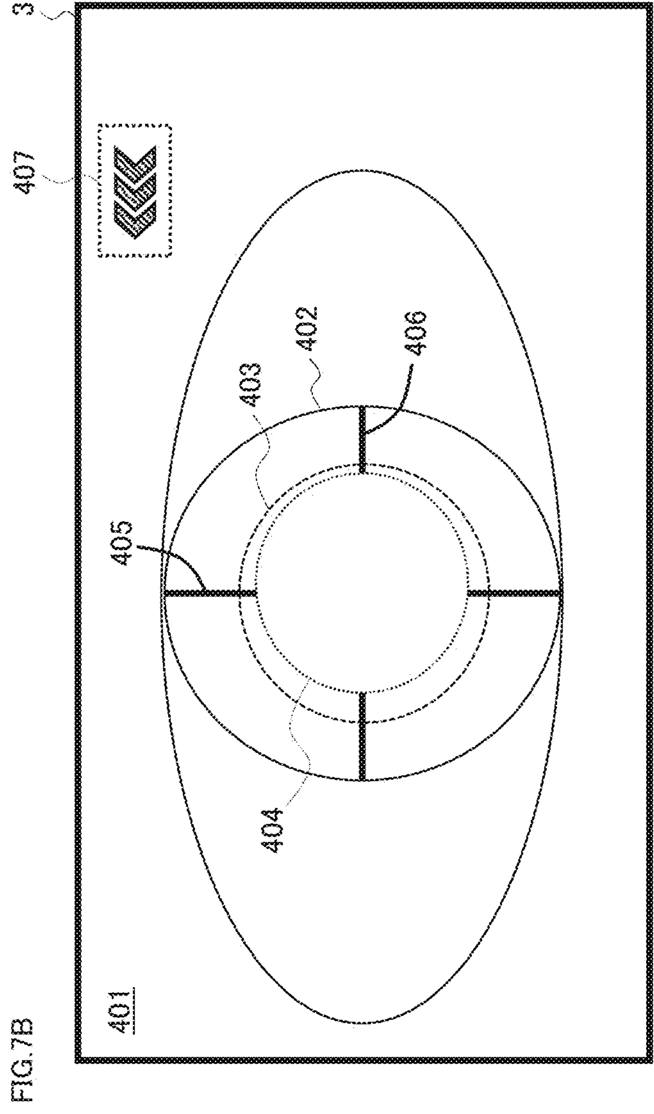
FIG. 7B is a diagram for describing an example of processing performed by an ophthalmic observation apparatus according to a modification example.

For example, as shown in FIG. 7A, the ophthalmic observation apparatus 1 is capable of displaying the live image 401 of the subject's eye on the display device 3, displaying the corneal ring image 402, the pupil edge image 403, and the intraocular lens outer edge image 404 on the live image 401, and further displaying the vertical line image 405 and the horizontal line image 406.

Both the vertical line image 405 and the horizontal line image 406 are arranged, for example, to pass through the center of the corneal ring image 402 having a circular shape or an elliptic shape. Note that only either one of the vertical line image 405 or the horizontal line image 406 may be displayed, a line image(s) oriented in an oblique direction may be displayed, or a line image that has a shape other than a straight line (e.g., a curved line) may be displayed. In some examples, the line image may be arranged to pass through the center of the pupil edge image 403 or may be arranged to pass through the center of the intraocular lens outer edge image 404.

By referring to such a line image(s) (e.g., the vertical line image 405 and the horizontal line image 406), the positional relationship between the corneal ring image 402 (the pupil edge image 403) and the intraocular lens outer edge image 404 can be automatically assessed. Also, the user can easily understand the positional relationship between the corneal ring image 402 (the pupil edge image 403) and the intraocular lens outer edge image 404 by referring to the line image(s).

The automatic assessment processing of the positional relationship between the corneal ring image 402 (the pupil edge image 403) and the intraocular lens outer edge image 404 includes a process of calculating a predetermined assessment parameter and a determination process based on the assessment parameter calculated. The assessment parameter may be, for example, either one of the degree of the uniformity of a distribution of the space (gap, distance) between the corneal ring image 402 (the pupil edge image 403) and the intraocular lens outer edge image 404, or the degree of the concentricity (or eccentricity) between the corneal ring image 402 (the pupil edge image 403) and the intraocular lens outer edge image 404.

The ophthalmic observation apparatus 1 may display, for example, guide information for uniformizing the space distribution (gap distribution, distance distribution) between the corneal ring image 402 (the pupil edge image 403) and the intraocular lens outer edge image 404, or guide information for increasing the degree of the concentricity. For example, as in FIG. 6I of the above embodiment example, the guide information 407 (including a group of arrow-shaped images) may be displayed that represents the direction in which the intraocular lens should be moved and the distance by which the intraocular lens should be moved. It should be noted that the guide information is not limited to the present example.

<Method of Controlling Ophthalmic Observation Apparatus>

Some embodiment examples (e.g., the ophthalmic observation apparatus 1 described above) provide a method of controlling an ophthalmic observation apparatus. It is possible to combine any items or matters relating to the ophthalmic observation apparatus 1 of the above embodiment examples with the example of the method described below.

An ophthalmic observation apparatus controlled by the method of an aspect example includes an optical system for generating a moving image of a subject's eye (e.g., the illumination optical system 30 and the observation optical system 40) and a processor (e.g., the controller 200 and the data processor 210). The method of the present aspect example first causes the optical system to generate a moving image of the subject's eye into which an artificial object has been inserted. Further, the method of the present aspect example causes the processor to analyze a still image included in the generated moving image to identify the first site image corresponding to a predetermined site of the subject's eye and the second site image corresponding to a predetermined site of the artificial object. In addition, the method of the present aspect example causes the processor to display, on a display device, the moving image generated, the first position information that represents a position of the first site image identified, and the second position information that represents a position of the second site image identified.

The method of the present aspect example is capable of achieving the same actions and effects as those of the ophthalmic observation apparatus 1 of the above embodiment examples. In addition, by combining any of the matters and items relating to the ophthalmic observation apparatus 1 of the above embodiment examples with the method of the present aspect example, the resulting method becomes capable of achieving the actions and effects corresponding to the combined matters and/or items.

<Program>

Some embodiment examples provide a program causing a computer to execute the method of the aspect example described above. It is possible to combine any of the matters and items relating to the ophthalmic observation apparatus 1 of the above embodiment examples with such a program.

The program thus configured is capable of achieving the same actions and effects as those of the ophthalmic observation apparatus 1 of the above embodiment examples. In addition, by combining any of the matters and items relating to the ophthalmic observation apparatus 1 of the above embodiment examples with the program, the resulting program is capable of achieving the actions and effects corresponding to the combined matters and/or items.

<Recording Medium>

Some embodiment examples provide a computer-readable non-transitory recording medium storing the program described above. It is possible to combine any of the matters and items relating to the ophthalmic observation apparatus 1 of the above embodiment examples with such a recording medium. The non-transitory recording medium may be in any form, and examples thereof include magnetic disks, optical disks, magneto-optical disks, and semiconductor memories.

The recording medium thus configured is capable of achieving the same actions and effects as those of the ophthalmic observation apparatus 1 of the above embodiment examples. In addition, by combining any of the matters and items relating to the ophthalmic observation apparatus 1 of the above embodiment examples with the recording medium, the resulting recording medium is capable of achieving the actions and effects corresponding to the combined matters and/or items.

The embodiments described in the present disclosure are merely examples, and any modification, omission, addition, substitution, etc. can be made within the scope of the present disclosure and its equivalents.

What is claimed is:

1. An ophthalmic observation apparatus for observing a subject's eye, comprising:

a surgical microscope configured to generate a moving image by photographing the subject's eye into which an intraocular lens has been inserted;

an analyzing processor configured to analyze a still image included in the moving image to identify a first site image corresponding to a predetermined site of the subject's eye and a second site image corresponding to a predetermined site of the intraocular lens; and a display controller circuit configured to display, on a display device, the moving image, first position information that represents a position of the first site image, and second position information that represents a position of the second site image, wherein the predetermined site of the subject's eve is an eye center position, the predetermined site of the intraocular lens is a center of the intraocular lens, and the display controller circuit is configured to display eye center position information that represents the eye center position as the first position information, display intraocular lens center position information that represents the center of the intraocular lens as the second position information, and display, based on the eye center position information and the intraocular lens center position, guide information for a user on the basis of a positional difference between the eye center position and the center of the intraocular lens.

2. The ophthalmic observation apparatus according to claim 1, wherein the display controller circuit is configured to display the guide information including first guide information that represents a movement direction of the intraocular lens.

3. The ophthalmic observation apparatus according to claim 2, wherein the display controller circuit is configured to display the guide information further including second guide information that represents a movement distance of the intraocular lens.

4. The ophthalmic observation apparatus according to claim 1, wherein the display controller circuit is configured to display the eye center position information and the intraocular lens center position information in mutually different aspects.

5. The ophthalmic observation apparatus according to claim 1, wherein the analyzing processor is configured to sequentially identify the eye center position and the center of the intraocular lens from still images sequentially generated by the surgical microscope, in parallel with generation of the moving image performed by the surgical microscope, and the display controller circuit is configured to sequentially update the eye center position information and the intraocular lens center position information displayed together with the moving image, in parallel with sequential generation of the still images performed by the surgical microscope and sequential analysis of the still images performed by the analyzing processor.

6. A method of controlling an ophthalmic observation apparatus including an optical system for generating a moving image of a subject's eye and a processor, the method comprising:

causing the optical system to generate a moving image of the subject's eye into which an intraocular lens has been inserted;

causing the processor to analyze a still image included in the moving image to identify a first site image corresponding to a predetermined site of the subject's eye and a second site image corresponding to a predetermined site of the intraocular lens;

causing the processor to display, on a display device, the moving image, first position information that represents a position of the first site image, and second position information that represents a position of the second site image, wherein the predetermined site of the subject's eye is an eye center position, and the predetermined site of the intraocular lens is a center of the intraocular lens;

displaying eye center position information that represents the eye center position as the first position information;

displaying intraocular lens center position information that represents the center of the intraocular lens as the second position information; and displaying, based on the eye center position information and the intraocular lens center position, guide information for a user on the basis of a positional difference between the eye center position and the center of the intraocular lens.

7. A computer-readable non-transitory recording medium storing a program causing a computer to execute the method of claim 6.

* * * * *